US012453812B2

(12) United States Patent
Haun et al.

(10) Patent No.: US 12,453,812 B2
(45) Date of Patent: Oct. 28, 2025

(54) INTEGRATED SYSTEM FOR MECHANICAL PROCESSING OF LIPOASPIRATE

(71) Applicant: THE REGENTS OF THE UNIVERSITY OF CALIFORNIA, Oakland, CA (US)

(72) Inventors: Jered Haun, Irvine, CA (US); Jeremy A. Lombardo, Irvine, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 995 days.

(21) Appl. No.: 17/617,301

(22) PCT Filed: Jun. 23, 2020

(86) PCT No.: PCT/US2020/039187

§ 371 (c)(1),
(2) Date: Dec. 7, 2021

(87) PCT Pub. No.: WO2020/263858

PCT Pub. Date: Dec. 30, 2020

(65) Prior Publication Data

US 2022/0249761 A1 Aug. 11, 2022

Related U.S. Application Data

(60) Provisional application No. 62/865,749, filed on Jun. 24, 2019.

(51) Int. Cl.

| | |
|---|---|
| ***A61M 1/00*** | (2006.01) |
| ***A61K 35/35*** | (2015.01) |
| ***B01L 3/00*** | (2006.01) |

(52) U.S. Cl.

CPC ............ *A61M 1/892* (2021.05); *A61K 35/35* (2013.01); *B01L 3/50273* (2013.01); (Continued)

(58) Field of Classification Search

CPC ......... A61K 35/35; A61M 1/79; A61M 1/892; B01L 2300/0681; B01L 2300/0864; (Continued)

(56) References Cited

U.S. PATENT DOCUMENTS

| | | | |
|---|---|---|---|
| 9,580,678 | B2 | 2/2017 | Haun et al. |
| 10,589,268 | B2 | 3/2020 | Zobi et al. |

(Continued)

FOREIGN PATENT DOCUMENTS

| | | | |
|---|---|---|---|
| CN | 107 649 059 | A | 2/2018 |
| CN | 109 975 265 | A | 7/2019 |

(Continued)

OTHER PUBLICATIONS

The extended European search report dated Oct. 4, 2022 for European Patent Appl No. 20830542.5, (7 pages).

(Continued)

*Primary Examiner* — Jennifer Wecker

(74) *Attorney, Agent, or Firm* — VISTA IP LAW GROUP LLP

(57) ABSTRACT

An integrated lipoaspirate processing system is disclosed for mechanically processing adipose tissue into a therapeutic material that, in some embodiments, may be directly injected into a subject. The system includes an emulsification device that is used to emulsify the lipoaspirate sample. The emulsified lipoaspirate is then filtered by a microfluidic filtration device. The filtrate of the microfluidic filtration device is then processed in a microfluidic dissociation device. The integrated platform or system helps standardize hydrodynamic processing of lipoaspirate by producing predictable and consistent shear forces and enabling automation in clinical settings. Progressive processing through multiple devices in series enables optimal recovery of regenerative cells while preventing clogging.

10 Claims, 20 Drawing Sheets

(52) U.S. Cl.
CPC . *B01L 3/502753* (2013.01); *B01L 2300/0681* (2013.01); *B01L 2300/0864* (2013.01)

(58) Field of Classification Search
CPC .......... B01L 3/50273; B01L 3/502753; B01L 3/502761; C12M 45/02; C12M 47/04
See application file for complete search history.

(56) References Cited

U.S. PATENT DOCUMENTS

| | | | | |
|---|---|---|---|---|
| 10,683,480 | B2 | 6/2020 | Haun et al. | |
| 10,722,540 | B1 | 7/2020 | Haun et al. | |
| 10,926,257 | B2 | 2/2021 | Haun et al. | |
| 11,130,127 | B2 | 9/2021 | Zobi et al. | |
| 2003/0161816 | A1 | 8/2003 | Fraser et al. | |
| 2004/0203136 | A1* | 10/2004 | Kellogg | B01F 33/30 435/287.2 |
| 2013/0171628 | A1* | 7/2013 | Di Carlo | C12M 29/00 435/7.1 |
| 2014/0377866 | A1 | 12/2014 | Haun et al. | |
| 2017/0131187 | A1 | 5/2017 | Haun et al. | |
| 2018/0056294 | A1 | 3/2018 | Di Carlo et al. | |
| 2018/0361382 | A1 | 12/2018 | Zobi et al. | |
| 2019/0070605 | A1 | 3/2019 | Haun et al. | |
| 2020/0164374 | A1 | 5/2020 | Zobi et al. | |
| 2020/0283723 | A1 | 9/2020 | Haun et al. | |
| 2021/0197191 | A1 | 7/2021 | Haun et al. | |
| 2021/0205810 | A1 | 7/2021 | Haun et al. | |

FOREIGN PATENT DOCUMENTS

| | | | |
|---|---|---|---|
| WO | WO 2013/075145 | A1 | 5/2013 |
| WO | 2017214323 | A1 | 12/2017 |
| WO | WO 2018/095511 | A1 | 5/2018 |
| WO | 2019232100 | A1 | 12/2019 |

OTHER PUBLICATIONS

Communication pursuant to Rules 70(2) and 70a(2) EPC dated Oct. 21, 2022 for European Patent Appl No. 20830542.5, (1 page).

PCT International Preliminary Report on Patentability (Chapter I of the Patent Cooperation Treaty) for PCT/US2020/039187, Applicant: The Regents of the University of California, Form PCT/IB/326 and 373, dated Jan. 6, 2022 (13 pages).

PCT International Search Report for PCT/US2020/039187, Applicant: The Regents of the University of California, Form PCT/ISA/210 and 220, dated Nov. 18, 2020 (6 pages).

PCT Written Opinion of the International Search Authority for PCT/US2020/039187, Applicant: The Regents of the University of California, Form PCT/ISA/237, dated Nov. 18, 2020 (11 pages).

Joel A. Aronowitz et al., Mechanical versus enzymatic isolation of stromal vascular fraction cells from adipose tissue, SpringerPlus (2015) 4:713.

Derek A. Banyard et al., Phenotypic Analysis of Stromal Vascular Fraction after Mechanical Shear Reveals Stress-Induced Progenitor Populations, Plastic and Reconstructive Surgery (Aug. 2016), 237e-247e.

Derek A. Banyard et al., Implications for human adipose-derived stem cells in plastic surgery, J. Cell. Mol. Med. vol. 19, No. 1, 2015 pp. 21-30.

Eleni Oberbauer et al., Enzymatic and non-enzymatic isolation systems for adipose tissue-derived cells: current state of the art, Cell Regeneration (2015) 4:7.

Xiaolong Qiu et al., Microfluidic device for mechanical dissociation of cancer cell aggregates into single cells, Lab Chip. Jan. 7, 2015; 15(1): 339-350.

Xiaolong Qiu et al., Microfluidic device for rapid digestion of tissues into cellular suspensions, Lab Chip. Sep. 26, 2017; 17(19): 3300-3309.

Xiaolong Qiu et al., Microfluidic filter device with nylon mesh membranes efficiently dissociates cell aggregates and digested tissue into single cells, Lab Chip. Sep. 11, 2018; 18(18): 2776-2786.

Xiaolong Qiu et al., Microfluidic channel optimization to improve hydrodynamic dissociation of cell aggregates and issue, Scientific Reports (2018) 8:2774.

Patrick Tonnard et al., Nanofat Grafting: Basic Research and Clinical Applications, Plast. Reconstr. Surg. 132: 1017, (2013).

Carlo Tremolada et al., Adipose Tissue and Mesenchymal Stem Cells: State of the Art and Lipogems® Technology Development, Curr Stem Cell Rep (2016) 2:304-312.

Min Zhu et al., Comparison of Three Different Fat Graft Preparation Methods: Gravity Separation, Centrifugation, and Simultaneous Washing with Filtration in a Closed System, Plast. Reconstr. Surg. 131: 873 (2013).

Response to Communication pursuant to Rules 70(2) and 70a(2) EPC dated May 2, 2023 for European Patent Application No. 20830542.5, (70 page).

* cited by examiner

INTEGRATED SYSTEM FOR MECHANICAL PROCESSING OF LIPOASPIRATE

RELATED APPLICATION

This Application is a U.S. National Stage filing under 35 U.S.C. § 371 of International Application No. PCT/US2020/039187, filed on Jun. 23, 2020, which claims priority to U.S. Provisional Patent Application No. 62/865,749 filed on Jun. 24, 2019, which is are hereby incorporated by reference. Priority is claimed pursuant to 35 U.S.C. §§ 119, 371 and any other applicable statute.

TECHNICAL FIELD

The technical field generally to systems and methods used to process lipoaspirate (also referred to sometimes herein as "LA"). In particular, the technical field generally relates to fluidic-based devices used to mechanically process lipoaspirate. In one particular embodiment, the system utilizes a number of stages to progressively mechanically process lipoaspirate including emulsification, filtration, and dissociation.

BACKGROUND

Interest is rapidly growing to utilize adipose tissue as a potent, easily accessible source of regenerative cells. Adipose-derived stem cells (ADSCs) are a subset of mesenchymal stem cells with adipogenic, osteogenic, and chondrogenic differentiation potential. Since discovery in 2001, ADSCs have been shown to improve regeneration in bone, cartilage, cardiac tissue, and other organs. Moreover, ADSCs have demonstrated potential in treating immune-mediated diseases including rheumatoid arthritis and Crohn's disease. Adipose tissue is typically obtained via tumescent liposuction, which fragments the sample into smaller pieces of tissue based on the dimensions of the cannula. The lipoaspirate (LA) is then digested enzymatically using collagenase and adipocytes are removed based on density. Finally, ADSCs are isolated from the resulting stromal vascular fraction (SVF) based on adherence to tissue culture flasks. Recently, attention has shifted to directly utilizing SVF to avoid tissue culture to decrease time and cost, as well as to avoid introduction of foreign components in culture media and potential phenotypic changes resulting from 2D culture on plastic. SVF comprises a diverse population including mature cells such as fibroblasts, endothelial cells, pericytes, and macrophages, regenerative cells such as mesenchymal stem cells (MSCs) and endothelial progenitor cells (EPCs), and contaminating blood cells. Importantly, SVF has been shown to exhibit comparable regenerative capabilities, including improved healing of burns, scars, and ischemic wounds in diabetes. SVF has also demonstrated therapeutic potential in models of multiple sclerosis, Crohn's disease, and diabetic foot ulcers. These regenerative properties have been attributed to the secretion of cytokines and growth factors that promote wound healing and angiogenesis, modulate the immune response, and reduce inflammation.

For clinical applications, another concern is that enzymatic digestion of adipose tissue using collagenase does not meet the Food and Drug Administrations (FDAs) guidelines for "minimal manipulation," and thus is classified as an experimental drug. This has led to the development of mechanical methods to liberate SVF from lipoaspirate without the use of enzymes. A common method involves repeatedly passing lipoaspirate back and forth between two syringes connected by a luer fitting, resulting in an emulsion termed "nanofat." See, e.g., Tonnard, P. et al. Nanofat grafting: basic research and clinical applications. *Plast Reconstr Surg* 132, 1017-1026 (2013). After a filtration step, nanofat has been injected through small-bore needles and shown to be effective in correcting superficial rhytides, scars, and discoloration, as well as improving neovascularization and fat graft survival. Recently the cellular composition of nanofat has been characterized where it was shown that stem and progenitor cell populations were enriched by mechanical stress in comparison to unprocessed lipoaspirate. See Banyard, D. A. et al. Phenotypic Analysis of Stromal Vascular Fraction after Mechanical Shear Reveals Stress-Induced Progenitor Populations. *Plast Reconstr Surg* 138, 237e-47e (2016). Specifically, an increase in the percentage of MSCs, EPCs, and a subset of MSCs called multilineage differentiating stress-enduring (MUSE) cells, which exhibit pluripotency were observed. Other mechanical methods have been developed, including centrifuging, shaking, and vortexing, as well as commercial methods such as LIPOGEMS®, REVOLVE™, and Puregraft®. For each of these methods, however, multiple manual processing steps are required that could result in poor standardization and repeatability.

SUMMARY

In one embodiment, an integrated fluidic device platform or system is disclosed for mechanically processing adipose tissue into a therapeutic material that may be delivered to a mammalian subject (e.g., by way of injection or the like). The integrated platform or system helps standardize hydrodynamic processing of lipoaspirate (LA) by producing predictable and consistent shear forces and enabling automation in clinical settings. Moreover, progressive processing through multiple devices or stages in series enables optimal recovery of regenerative cells while preventing clogging. In one particular embodiment, a first stage of the system or platform uses an emulsification device to process the LA. This emulsification device replaces the prior inter-syringe method used to produce nanofat, whereby LA is passed back-and-forth between connected syringes. SVF generated by the emulsification device matches or exceeds nanofat in terms of total cell numbers, as well as key stem and progenitor cell populations including DPP4+/CD26+ cells which are known to improve wound healing.

Subsequent to the first stage of processing (i.e., processing with the emulsification device), the emulsified lipoaspirate then passes to a second stage, namely a microfluidic filtration device that receives emulsified lipoaspirate. The microfluidic filtration device is a microfluidic-based device that includes separate channels or fluid-containing regions (e.g., chamber) that incorporate a filter membrane interposed between the separate channels or fluid-containing regions to filter out larger tissue aggregates. In particular, a multi-layer microfluidic device is used in which different channels and/or chambers are located in different layers of a substrate material (e.g., acrylic) and separated from one another by a filter membrane. The different layers are stacked on one another and bonded or otherwise adhered to one another to form the final multi-layer microfluidic device. In one particular embodiment, the filter membrane is a polyamide-based (e.g., Nylon®) mesh membrane that has pore sizes to exclude larger tissue fragments and cellular aggregates. In one particular embodiment, the pore sizes of the filter membrane are within the range of about 100 μm and about 5,000 μm, and more preferably within the range of about 250 μm to 2,500 μm. For example, a pore size of around 1,000 μm was found to work well.

Because the size of the filter membrane in some embodiments is relatively large, the filter membrane may be supported by a substrate layer that incorporates a support grid located underneath the filter membrane that prevents sagging or collapse of the filter membrane. Smaller sized cells and aggregates can pass through the filter membrane and exit the microfluidic device via a dedicated outlet. Larger sized aggregates and like that do not pass through the filter membrane exit the microfluidic device via a secondary outlet, when optionally present. It was found that passing emulsified sample through the microfluidic filter device generally maintains total cell numbers and relative cell numbers for progenitor/stem populations. Conversely, passing nanofat through a standard 1 mm mesh cloth resulted >2-fold reduction of total cells recovered, as well as a decrease in the relative number of MSCs and EPCs.

Finally, after processing/filtration with the microfluidic device, a third stage is provided that utilizes a microfluidic dissociation device to further break down tissue aggregates remaining after the filtration device. The microfluidic tissue dissociation device includes a plurality of branched microfluidic channels that branch into progressively smaller (width-wise) channels followed by a number of additional branched microfluidic channels of increasing width. For example, from going from inlet to outlet, a first channel bifurcates to two smaller channels which then bifurcate again to four even smaller channels. The four branch channels then recombine (in reverse fashion) where the four channels become two channels with increasing width which combine to a single channel with a larger width. Within the individual channels/branch channels are a plurality of constriction and expansion regions along a length thereof to aid in tissue dissociation. The dissociation device did not significantly affect total cell recovery, but did provide for an enrichment of CD34+ cells and EPCs that was dose dependent with flow rate. Some cells did decrease in a dose-dependent manner, however.

The lipoaspirate may be run through the respective stages of the system (i.e., emulsification (first stage), filtration (second stage), dissociation (third stage)) using one or more pumps such as syringe pumps. For example, a set of syringe pumps may be used to flow the lipoaspirate through the emulsification device back-and-forth a number of times. These same pumps (or another set of pumps) may then run the output of the emulsification device into the microfluidic filtration device. Likewise, the same pumps (or another set of pumps) may then pump the output of the microfluidic filtration device through the microfluidic dissociation device. The lipoaspirate from the microfluidic filtration device may be passed through the microfluidic dissociation device for a plurality of passes. The final processed lipoaspirate can then be directly used by the physician or other healthcare provider. For example, the final processed lipoaspirate can be loaded into a syringe or other delivery device and injected directly into tissue.

In one embodiment, an emulsification device for processing lipoaspirate includes a substrate having an inlet and an outlet and a fluid passageway extending between the inlet and the outlet. A first constriction region is formed in the fluid passageway adjacent to the inlet. A second constriction region is formed in the fluid passageway adjacent to the outlet. An expansion region is formed in the fluid passageway between the first constriction region and the second constriction region.

In another embodiment, a method of processing lipoaspirate includes providing an emulsification device for processing lipoaspirate. The emulsification device includes a substrate having an inlet and an outlet and a fluid passageway extending between the inlet and the outlet; a first constriction region formed in the fluid passageway adjacent to the inlet; a second constriction region formed in the fluid passageway adjacent to the outlet; and an expansion region formed in the fluid passageway between the first constriction region and the second constriction region. A microfluidic filtration device is provided that includes an inlet fluidically coupled to a microfluidic chamber or channel; a filter membrane interposed between the microfluidic chamber or channel and a second microfluidic channel disposed in the microfluidic filtration device, wherein the second microfluidic channel is in fluidic communication with the microfluidic chamber or channel via pores formed in the filter membrane; and an outlet coupled to a downstream location of the second microfluidic channel. The lipoaspirate is then passed (e.g., pumped) between the inlet and outlet of the emulsification device a plurality of times to generate emulsified lipoaspirate. The emulsified lipoaspirate is then passed (e.g., pumped) into the inlet of the microfluidic filtration device. The filtered emulsified lipoaspirate is then collected from the outlet of the microfluidic filtration device. The filtered emulsified lipoaspirate may then be run through a microfluidic dissociation device, in some embodiments. Thus, the method of processing lipoaspirate includes serially processing lipoaspirate with an emulsification device, microfluidic filtration device, and microfluidic dissociation device.

In another embodiment, a system for processing lipoaspirate includes an emulsification device, a microfluidic filtration device, and a microfluidic dissociation device. The emulsification device for processing lipoaspirate includes a substrate having an inlet and an outlet and a fluid passageway extending between the inlet and the outlet; a first constriction region formed in the fluid passageway adjacent to the inlet; a second constriction region formed in the fluid passageway adjacent to the outlet; and an expansion region formed in the fluid passageway between the first constriction region and the second constriction region. The microfluidic filtration device includes an inlet coupled to a chamber or channel at an upstream location; a filter membrane interposed between the chamber or channel and a second microfluidic channel, wherein the second microfluidic channel is in fluidic communication with the chamber or channel via pores in the filter membrane; and an outlet coupled to a downstream location of the second microfluidic channel. The microfluidic dissociation device includes an inlet coupled to an inlet microfluidic channel that branches into a plurality of downstream branch channels having decreased dimensions; an outlet coupled to an outlet microfluidic channel that branches into a plurality of upstream branch channels that connect to the downstream branch channels, wherein upstream branch channels have decreased dimensions in the upstream direction, wherein the inlet microfluidic channel, outlet microfluidic channel and the plurality of upstream and downstream branch channels comprise a plurality of expansion and constriction regions extending along a length of the respective channels.

DETAILED DESCRIPTION OF THE ILLUSTRATED EMBODIMENTS

Figure 1:
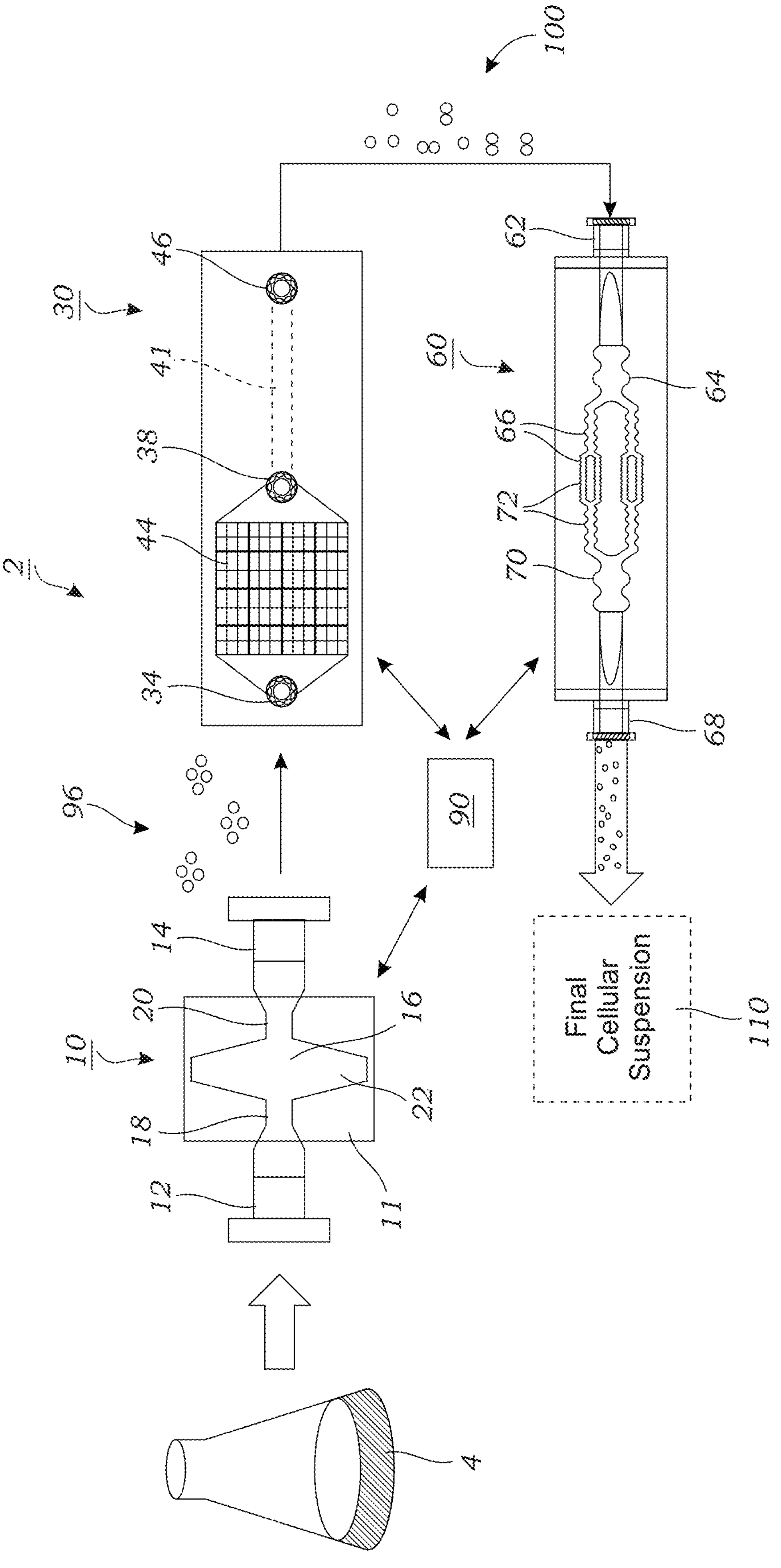
FIG. 1 illustrates one embodiment of a system for processing lipoaspirate. Lipoaspirate is processed in a serial manner first by an emulsification device followed by a microfluidic filtration device and finally a microfluidic dissociation device. Lipoaspirate is first broken down into smaller tissue aggregates using the emulsification device. Sample is then passed through the lipoaspirate filter device to remove the largest tissue pieces, which would clog injection needles or downstream device channels. Finally, the smaller tissue fragments will be passed through the lipoaspirate dissociation device, where higher levels of shear force will be applied to further break down tissue and optimally activate resident stem and progenitor cell populations. Following processing with these three devices, the final cellular suspension is collected and can be injected directly into a patient for wound healing or other regenerative therapies.

FIG. 1 illustrates a system 2 for processing lipoaspirate 4 according to one embodiment. The lipoaspirate 4 may be obtained by, for example, liposuction of a mammalian subject, although other retrieval methods may be used. The lipoaspirate 4 that is processed and then used (e.g., injected back into the tissue of the mammalian subject) is typically used from the same subject. As seen in FIG. 1, a series of devices including an emulsification device 10, microfluidic filtration device 30, and microfluidic dissociation device 60 are used to serially process the lipoaspirate 4 into the final state 110 (e.g., final cellular suspension) which can then be used for tissue injections or other applications. The first device 10 to process the lipoaspirate 4 is an emulsification device 10. The emulsification device 10 emulsifies the lipoaspirate 4 to generate emulsified lipoaspirate 96. As seen in FIG. 1, one or more pumps 90 are provided to operate the emulsification device 10, microfluidic filtration device 30, and microfluidic dissociation device 60. As explained herein, the emulsification device 10, microfluidic filtration device 30, and microfluidic dissociation device 60 may have their own dedicated pump(s) 90. Alternatively, the pump(s) 90 may be shared across all or multiple devices 10, 30, 60. For example, an integrated system 2 may share pumps 90 across all devices 10, 30, 60 with appropriate valves and conduits connecting the devices 10, 30, 60.

With reference to FIGS. 1, 3, 4A, 4B, the emulsification device 10 is formed in a substrate 11, which in one embodiment, is a monolithic substrate 11 that is fabricated using three-dimensional printing or other additive manufacturing techniques. A biocompatible polymer is used for the monolithic substrate 11 such as Somos® BioClear available from DSM (Elgin, Illinois, USA). The emulsification device includes an inlet 12 and an outlet 14 (these may be designed as luer inlets/outlets) and fluid passageway 16 formed therein between the inlet 12 and the outlet 14 (also seen in FIGS. 3 and 4B). A first constriction region 18 is formed in the fluid passageway 16 adjacent to the inlet 12 while a second constriction region 20 is formed in the fluid passageway 16 adjacent to the outlet 14. The first and second constriction regions 18, 20 are regions of the fluid passageway that have reduced cross-sectional areas (e.g., reduced diameter) as compared to the remainder of the fluid passageway 16. In one embodiment, the first and second constriction regions 18, 20 have cross-sectional dimensions of between 1 mm and 2 mm. In other embodiments, the cross-sectional dimension of the first and second constriction regions 18, 20 may be between about 200 μm and about 5 mm. The cross-sectional dimensions of the first and second constriction regions 18, 20 may be the same as each other (preferred) or different.

Figure 3:
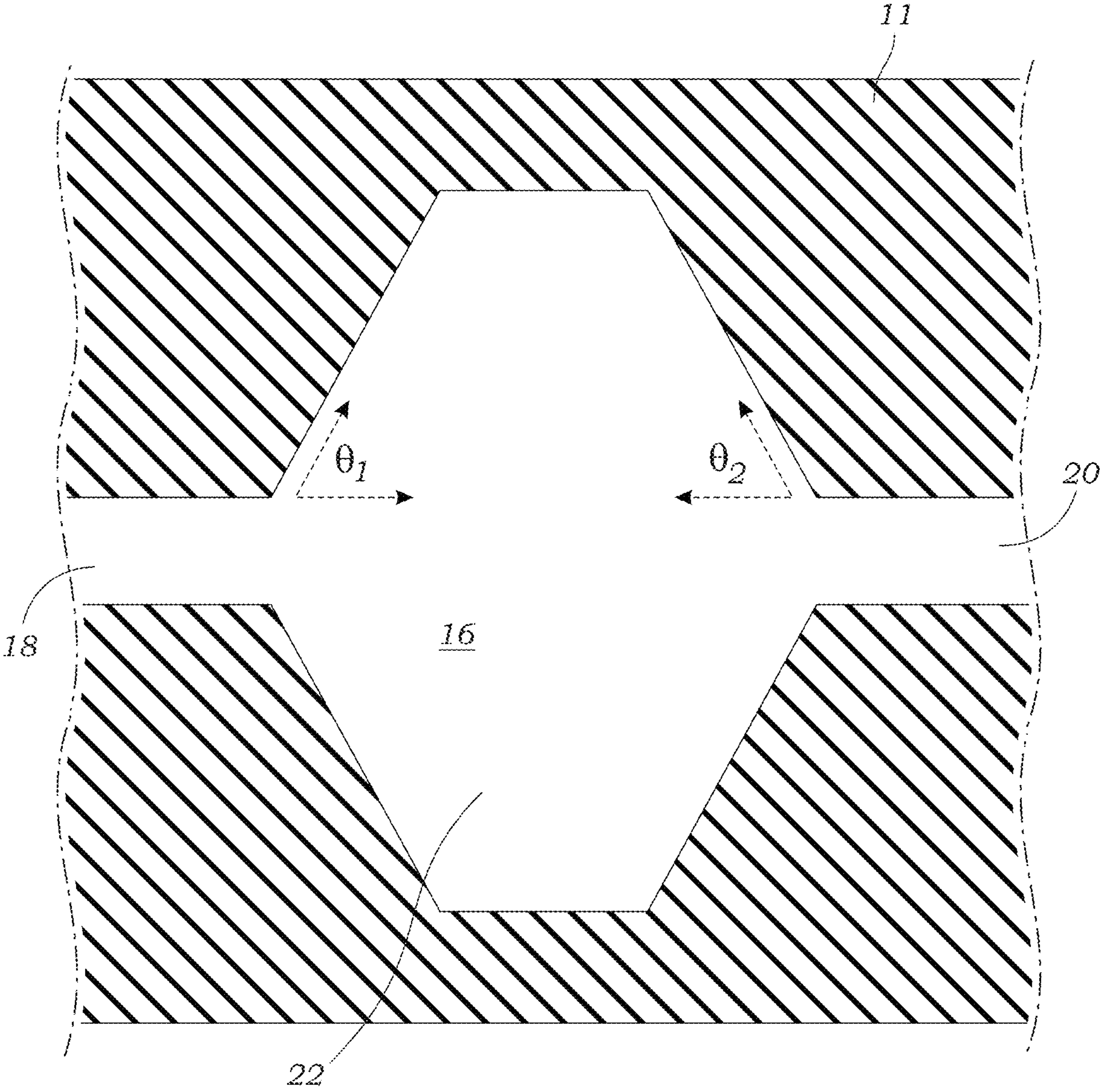
FIG. 3 illustrates a cross section of the emulsification device showing the first and second constrictions and the expansion region.
Figure 4A:
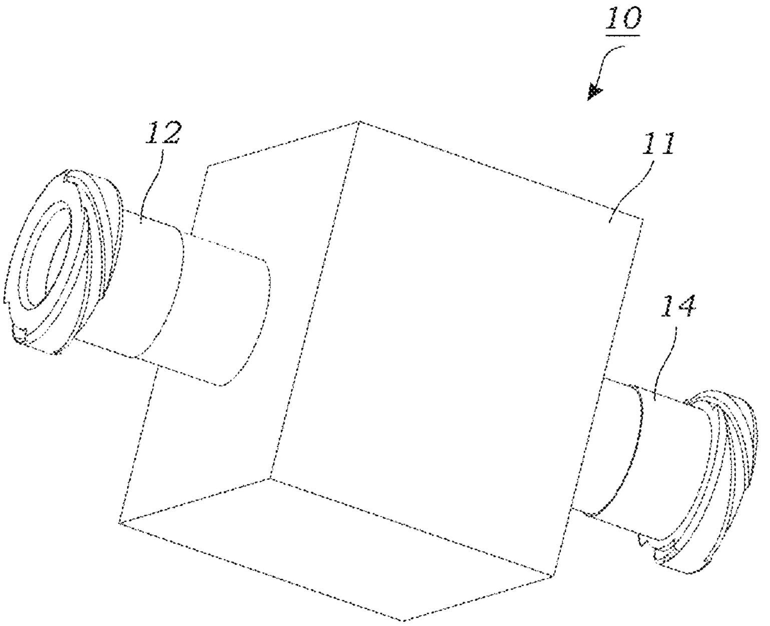
FIG. 4A illustrates a perspective view of one embodiment of an emulsification device.
Figure 4B:
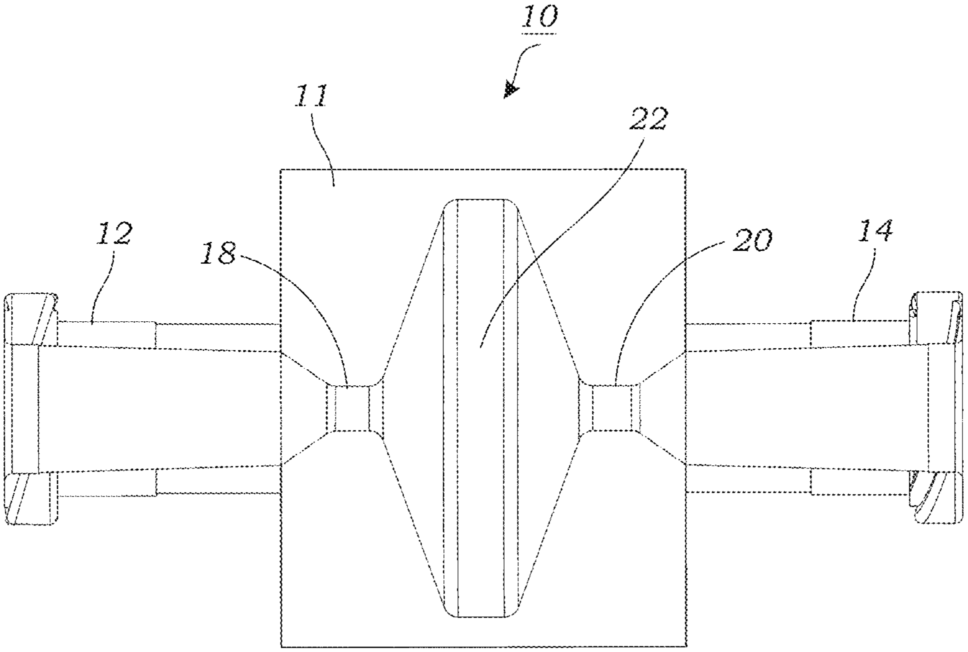
FIG. 4B illustrates cross-sectional view of the emulsification device of FIG. 4A.

As best seen in FIGS. 3 and 4B, an expansion region 22 is formed in the fluid passageway 16 between the first constriction region 18 and the second constriction region 20 and is an abrupt expansion of the fluid passageway 16 to a maximum cross-sectional dimension, that in one embodiment, is within the range of about 10 mm to about 20 mm (for example, a 14 mm width of the expansion region 22 and 1.5 mm for the first and second constriction regions 18, 20). In still other embodiments, the expansion region 22 may range from about 500 μm and about 30 mm. The expansion region 22 is typically substantially larger than the first and second constriction regions 18, 20 so that, as explained below, turbulent mixing conditions are present within the expansion region 22. In one embodiment, and with reference to FIG. 3, the abrupt expansion of the expansion region 22 is formed by an angled wall or surface that rapidly expands outwardly. An angle $\theta_1$ is formed by the expanding wall or surface that defines the expansion region 22. In one embodiment, this angle $\theta_1$ may be around 70°. The abrupt expansion is followed by an abrupt decrease by an angled wall or surface as illustrated in FIG. 3. An angle $\theta_2$ is formed by the contracting wall or surface that defines the expansion region 22. In one embodiment, this angle $\theta_2$ may be around 70°. Thus, in one particular implementation, $\theta_1$ is equal to $\theta_2$ (i.e., a symmetrical construction). It should be appreciated, however, that other angles for $\theta_1$, $\theta_2$ may be used. The key is the generation of turbulent mixing conditions in the expansion region 22. In addition, the first and second constrictions 18, 20 and the expansion region 22 may be formed in multiple planes (i.e., the angled wall or surface extends in three dimensions), for example, through additive manufacturing techniques (e.g., 3D printing). The cross-sectional shape of the first and second constrictions 18, 20 and the expansion region 22 may be circular, although other shapes are contemplated.

Importantly, the first and second constrictions 18, 20 and the expansion region 22 are designed such that the lipoaspirate 4 experiences high shear forces while traversing the first and second constrictions 18, 20 and the lipoaspirate 4 undergoes turbulent mixing while in the expansion region 22. The large size of the expansion region 22 relative to the size of the first and second constrictions 18, 20 encourages the turbulent mixing which promotes the emulsification of the lipid contents of the lipoaspirate 4. Typical flow rates for flowing the lipoaspirate 4 through the emulsification device includes flow rates within the range of about 1 mL/s to about 50 mL/s are typical (e.g., 20 mL/s). The lipoaspirate 4 is pumped through the emulsification device 10 by a pump 90 such as that illustrated in FIGS. 1 and 2A. The lipoaspirate 4 may make a number of passes through the emulsification device 10. A single pass of lipoaspirate 4 is lipoaspirate 4 passing from inlet 12 to outlet 14 (or vice versa). A typical number of passes through the emulsification device 10 is between about ten (10) and about thirty (30) passes although more or less passes may be used.

Figure 5A:
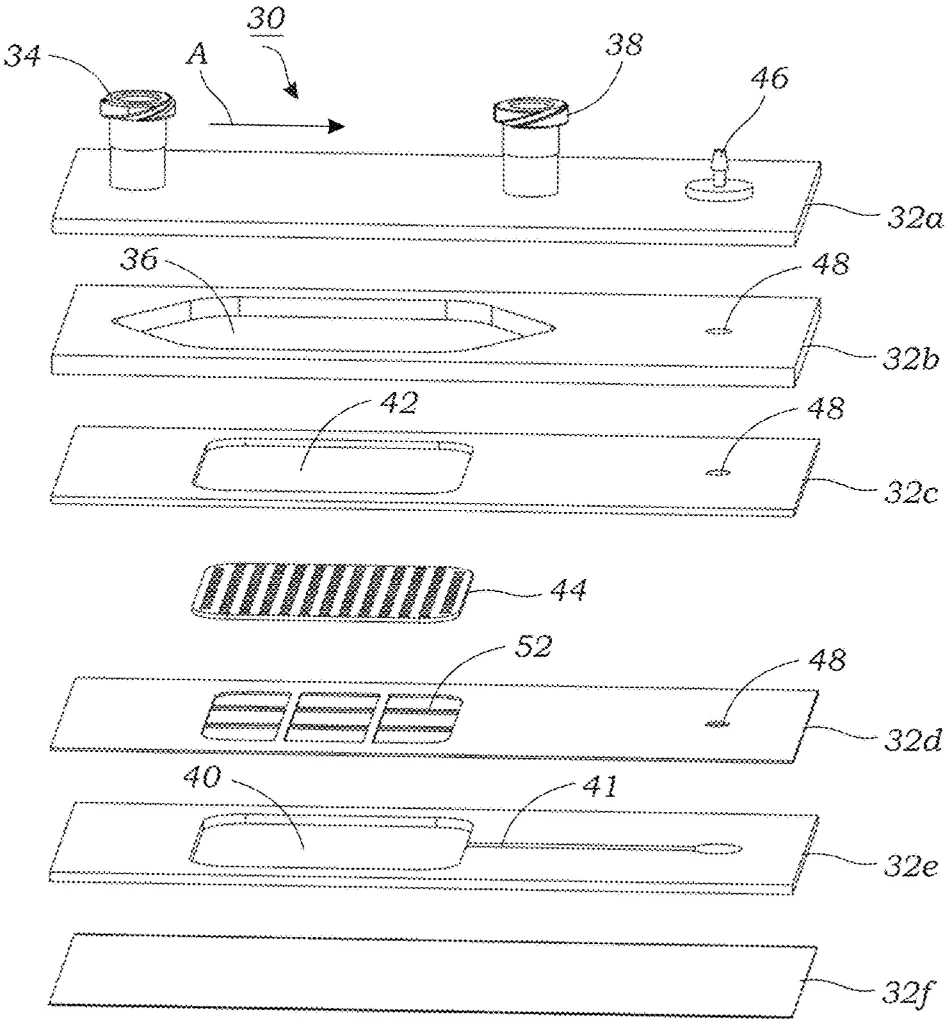
FIG. 5A illustrates an exploded view of a filtration device showing six hard plastic layers, including two layers that have a chamber or fluid channel, filter spacer layer and support grid layer, and two layers sealing the top and bottom of the device. The filter is interposed between the support grid layer and the filter spacer layer.
Figure 5B:
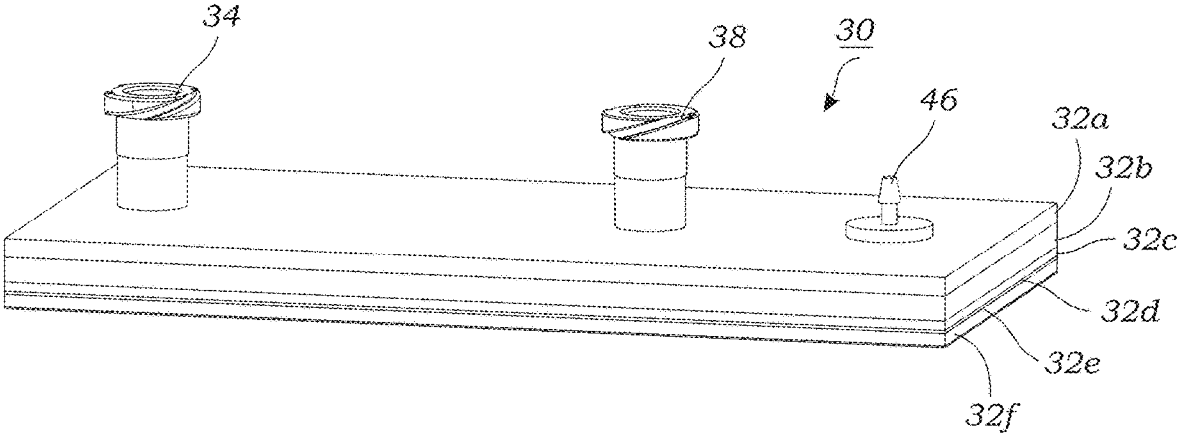
FIG. 5B illustrates a perspective view of the fully assembled microfluidic filtration device of FIG. 5A.

The second stage of the system 2 is a microfluidic filtration device 30 as seen in FIGS. 1, 5A, and 5B. The microfluidic filtration device 30 may be formed in one or more substrates or layers 32*a*-32*f* as best illustrated FIGS. 5A and 5B. The substrates or layers 32*a*-32*f* may be formed from a polymer or plastic material that contains various features formed therein that are subsequently laminated or otherwise bonded together to form the final microfluidic filtration device 30 according to one embodiment. The various features formed in the substrates or layers 32*a*-32*f* include the channels, chambers, and fluid passageways (described below in more detail) through which fluid (containing the tissue/cells) flows during operation of the microfluidic filtration device 30.

The microfluidic filtration device 30 includes an inlet 34 through which fluid flows into the microfluidic tissue filtration device 30. The inlet 34 may include a barbed end or the like as illustrated that can be connected to tubing or other conduit that is used to deliver the fluid containing the processed tissue from the emulsification device 10 to the microfluidic filtration device 30. The inlet 34 is fluidically coupled to a large channel or chamber 36 at an upstream location (arrow A of FIG. 5A indicates the direction of fluid flow). The large channel or chamber 36 is, in one embodiment, fluidically coupled to an outlet 38 formed in substrate or layer 32*a* that is located at a downstream location. This outlet 38 is, however, optional and may be omitted or purposely plugged. The outlet 38 may include a barbed end or the like as illustrated that can be connected to tubing or other conduit that is used to remove fluid containing cells and cell aggregates from the microfluidic tissue filtration device 30. The large channel or chamber 36 is at least partially defined in one or more of the substrates or layers 32*a*-32*c*. For example, the surfaces (top, bottom, sides) of the large channel or chamber 36 may be defined in the one or more of the substrates or layers 32*a*-32*c*. With reference to FIG. 5A, substrate or layer 32*a* forms the top while substrate or layer 32*b* (and to some extent substrate or layer 32*c*) may form the sides of the large channel or chamber 36. The bottom of the large channel or chamber 36 is defined by a filter membrane 44 as discussed herein.

The typical cross-sectional dimension of the large channel or chamber 36 may include a height within the range of about 1 mm to about 10 mm and a width within the range of about 1 cm to about 10 cm. The length of the large channel or chamber 36 (from end to end) may vary from a few centimeters and tens or even hundreds of centimeters (e.g., from about 5 cm to about 100 cm in one example). An example of the dimensions of the large channel or chamber 36 may include a height of around 2 mm, a width of around 30 mm, and a length of around 45 mm. It should be appreciated that these dimensions are illustrative.

With reference to FIG. 5A, the microfluidic tissue filtration device 30 includes a second chamber or channel 40 that resides in substrate or layer 32*e*. The second chamber or channel 40 is located on the other side of a filter membrane 44 (opposite from chamber or channel 36). The second chamber or channel 40 also includes a narrow channel 41 that extends along a length of the substrate or layer 32*e* and provides a fluidic path towards outlet 46 as explained herein. In this regard, the second chamber or channel 40 is located in a different plane than the large channel or chamber 36. For example, the second chamber or channel 40 may be located in a lower plane (i.e., substrate or layer 32*e*) than the large channel or chamber 36 (i.e., substrate or layer 32*b*). Like the large channel or chamber 36, the second chamber or channel 40 may be defined in the one or more of the substrates or layers 32*e*.

The typical cross-sectional dimension of the second chamber or channel 40 may include a height within the range of about several hundred micrometers to about 10 mm and a width within the range of about 1 mm to about 10 cm. The length of the second chamber or channel 40 (from end to end) may vary from a few centimeters and tens or even hundreds of centimeters (e.g., from about 5 cm to about 100 cm in one example). As best seen in FIG. 5A, second chamber or channel 40 has a wide region (upstream) and a narrow channel 41 (downstream). An example of the dimensions of a second chamber or channel 40 may include a height of around 1 mm, a width of around 30 mm in the widest portion and around 2 mm in the narrower region 41 and a length of around 60 mm. It should be appreciated that these dimensions are illustrative.

With reference to FIG. 5A, the filter membrane 44 is disposed on substrate or layer 32*e* that includes a grid layer 52 therein. The grid layer 52 includes a number of holes, apertures, or spaces that pass completely through the substrate or layer 32*e* while various ribs form a physical grid layer 52 on which the filter membrane 44 resides. The filter membrane 44 may be formed as a single layer of woven mesh polymer thread that is disposed on the grid layer 52 of substrate or layer 32*e*. An adhesive may be used to adhere the filter membrane 44 to the grid layer 52. In one embodiment, the thread used for the filter membrane 44 is polyamide thread (e.g., Nylon®). In one particular embodiment, the pore diameters of the filter membrane 44 are within the range of about 100 μm and about 5,000 μm, and more preferably within the range of about 250 μm to 2,500 μm. For example, a pore diameter of around 1,000 μm was found to work well. Pore diameters in this context refers to the nominal or average pore diameter of the particular filter membrane 44. The size of the membrane 44 may vary but in order to process high volume of lipoaspirate 4 the membrane 44 has a length/width that is several to tens of centimeters in size. A spacer substrate or layer 32*c* is disposed atop the substrate or layer 32*e* and includes an aperture 42 that accommodates the filter membrane 44.

A bottom substrate or layer 32*f* forms the bottom of the microfluidic tissue filtration device 30. The bottom substrate or layer 32*f* defines the bottom of the second chamber or channel 40 and narrow channel 41. In the fully assembled microfluidic tissue filtration device 30, fluid that enters the inlet 34 and cells or cell clusters small enough to pass through the pores of the filter membrane 44 enter the large channel or chamber 36 and then are able to pass through the filter membrane 44. These cells or cell clusters enter the second chamber or channel 40 located on the opposing side of the filter membrane 44 and proceed down the narrow channel 41. An outlet 46 located in substrate or layer 32*a* is fluidically coupled the narrow channel 41 by way of vias or apertures 48 located in substrate or layers 32*b*, 32*c*, 32*d*. The outlet 46 may optionally include a barbed end or the like that can be connected to tubing or other types conduit. In other alternative embodiments, additional filter membranes and microfluidic channels may be added to provide additional layers of filtering. Examples of such microfluidic tissue filtration devices are described in PCT Patent Application No. PCT/US19/34470 (International Publication No. WO/2019/232100), which is incorporated herein by reference.

The microfluidic tissue filtration device 30 may be fabricated using a commercial laminate approach, with channel features (including chambers, channels, apertures, vias or holes) laser micro-machined into hard plastic (e.g., polyethylene terephthalate, PET). This provides a more robust device than alternative fabrication methods, such as photolithography and casting of polydimethyl siloxane (PDMS), and thus better supports the high flow rates and pressures that are desired for rapid tissue filtration. Individual layers

32*a*-32*f* of the microfluidic tissue filtration device 30 may be assembled by stacking (along with the membrane 44) and an adhesive is used to bond the layers 32*a*-32*f* together using pressure lamination. The microfluidic tissue filtration device 30 may also be formed as a monolithic structure in other embodiments.

Figure 6A:
FIG. 6A illustrates a perspective view of one embodiment of a microfluidic dissociation device.
Figure 6B:
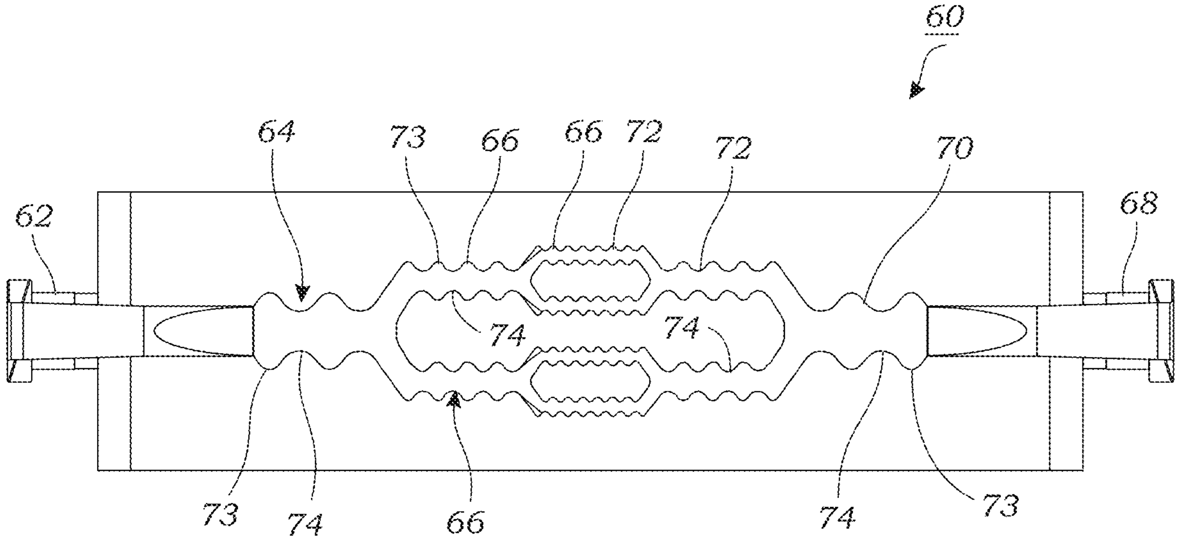
FIG. 6B illustrates a cross-sectional view of the microfluidic dissociation device of FIG. 6A.

The output of the microfluidic tissue filtration device 30 (i.e., the output from outlet 46) then passes to the microfluidic dissociation device 60 as described herein. The microfluidic dissociation device 60 is illustrated in FIGS. 1, 6A, 6B. The microfluidic dissociation device 60 includes an inlet 62 that is coupled to an inlet microfluidic channel 64 that branches into a plurality of downstream branch channels 66 having decreased dimensions. An outlet 68 is coupled to an outlet microfluidic channel 70 that branches (when going in the upstream or reverse direction through the microfluidic tissue filtration device 30) into a plurality of upstream branch channels 72 that connect to the downstream branch channels 66 and have increased dimension toward the outlet 68. For example, the inlet microfluidic channel 64 bifurcates to two (2) branch channels 66 (of reduced width) which branch again to four (4) branch channels 66 (of reduced width). These branch channels 66 connect to branch channels 72 (or are a continuation thereof) which then recombine to two channels (of increasing width) following by another recombination to a single outlet microfluidic channel 70 (of increasing width).

The inlet microfluidic channel 64, outlet microfluidic channel 70 and the plurality of upstream and downstream branch channels 66, 72 comprise a plurality of expansion regions 73 and constriction regions 74 extending along a length of the respective channels 66, 72. The expansion regions 73 and constriction regions 74 are formed within the respective channels 66, 72 and are alternating regions where the width of the channel(s) 66, 72 increases and decreases. The expansion regions 73 and constriction regions 74 generate fluidic jets of varying size scales and magnitudes to help break down tissue fragments and cell aggregates using hydrodynamic shear forces. The design of the expansion regions 73 and constrictions regions 74 enables gradual disaggregation, thereby maximizing cell yield without causing extensive cell damage. An example of a similar microfluidic dissociation device 60 may be found in U.S. Pat. No. 9,580,678 which is incorporated herein by reference. The microfluidic dissociation device 60 may be made as a layered structure out of hard plastic or a polymer (e.g., acrylic) that is bonded together to form the final device. For example, the fluidic microchannels 66, 72 may be laser cut and bonded together with apertures or vias connecting various layers being formed in the layers. The layers may be bonded by use of an adhesive and pressure bonding. The output of the microfluidic dissociation device 60 is the final processed lipoaspirate 4 which may be injected or otherwise applied to mammalian tissue.

With reference to FIG. 6B, the inlet microfluidic channel 64 and the outlet microfluidic channel 70 are single microfluidic channels that contain expansion regions 73 and constriction regions 74. The height of the inlet microfluidic channel 64 and the outlet microfluidic channel 70 as well as the branch channels 66, 72 is, in one embodiment, around 750 μm. The expansion regions 73 in the inlet microfluidic channel 64 and the outlet microfluidic channel 70 have a width of around 9 mm in one embodiment. The constriction regions 74 in the inlet microfluidic channel 64 and the outlet microfluidic channel 70 have a width of around 3 mm in one embodiment (expansion region 73 is about three times as wide as the constriction regions 74). The inlet microfluidic channel 64 and the outlet microfluidic channel 70 bifurcate into two branch channels 66, 72, respectively as seen in FIG. 6B. The expansion regions 73 in these first branch channels 66, 72 have a width of around 4.5 mm while the constriction regions 74 have a width of around 1.5 mm. These two branch channels 66, 72 then bifurcate again to form four (4) branch channels 66, 72 as seen in FIG. 6B. The expansion regions 73 in these four (4) branch channels 66, 72 have a width of around 2.25 mm while the constriction regions 74 have a width of around 750 μm. While the four (4) branch channels 66, 72 illustrated in FIG. 6B are described using different reference numbers herein, it should be understood that these four (4) channels need not be separate channels but may form four separate continuous channels. The use of two reference numerals is for convenience sake when describing the fluidic structure and these smallest branch channels may be referred to as branch channels 66 and/or branch channels 72.

Figure 2A:
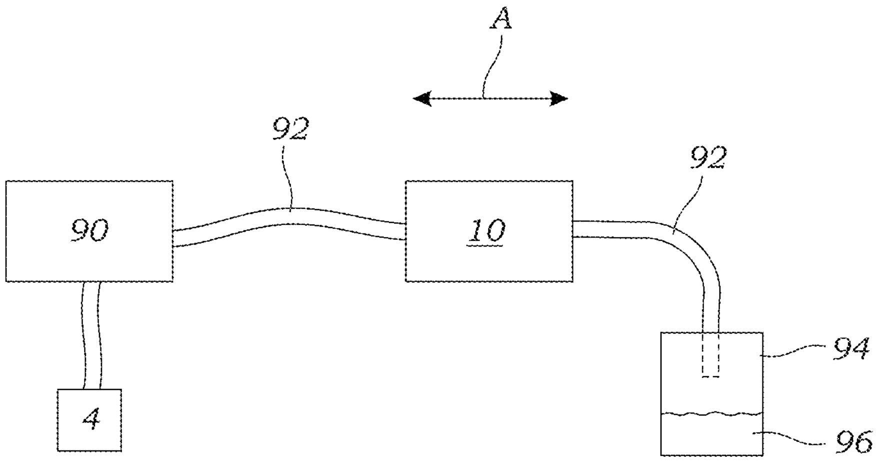
FIG. 2A schematically illustrates how a pump is used to pump lipoaspirate through the emulsification device (i.e., emulsification).

With reference to FIG. 1 and FIGS. 2A-2C, the lipoaspirate 4 is first pumped through the emulsification device 10 for a plurality of passes. FIG. 2A illustrates a pump 90 that is fluidically coupled to the emulsification device 10 via tubing or conduit 92 and pumps the lipoaspirate 4 bidirectionally through the emulsification device 10. Arrow A in FIG. 2A illustrates how the lipoaspirate 4 can move in both directions through the emulsification device 10. In the forward direction, the processed lipoaspirate 4 may proceed through the emulsification device 10 and into a container 94 (which in some embodiments may also be a syringe). The processed lipoaspirate 4 may then be run through the emulsification device 10 for another "pass", for example, by reversing the flow direction of the pump 90 (e.g., using a syringe pump or the like to pull fluid (and cells) through the emulsification device 10). This forward and reverse process may take place for a plurality of passes. FIG. 1 illustrates the emulsified lipoaspirate 96 that ultimately results from processing with the emulsification device 10.

Figure 2B:
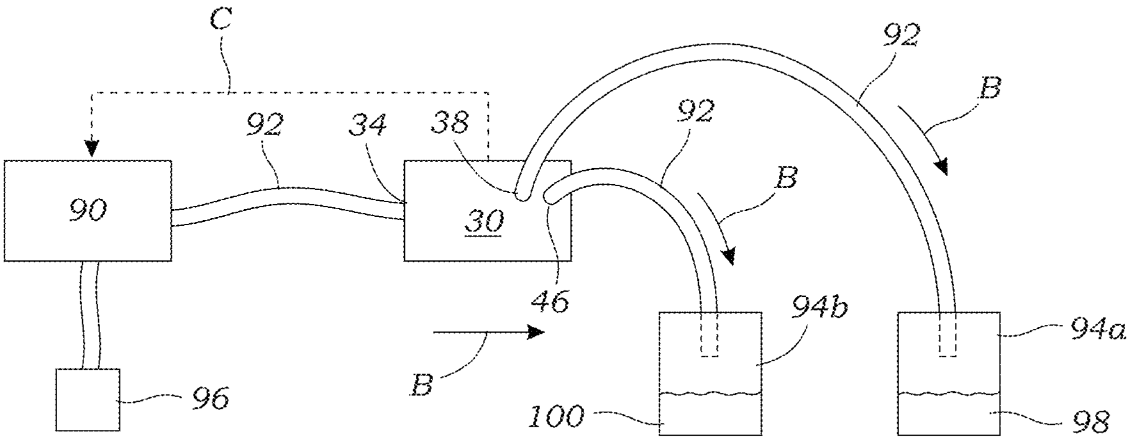
FIG. 2B schematically illustrates how a pump is used to pump lipoaspirate through the lipoaspirate filter device (i.e., filtration).

FIG. 2B illustrates emulsified lipoaspirate 96 from the emulsification device 10 being pumped via pump 90 through the microfluidic tissue filtration device 30. A portion of the emulsified lipoaspirate 96 that includes larger pieces of tissue or large clusters of cells which cannot pass through the filter membrane 44, exits via the outlet 38 (i.e., secondary optional outlet) of the microfluidic tissue filtration device 30 when optionally present. If not present, larger pieces of tissue or larger clusters of cells may remain in chamber or channel 36 or they may accumulate on the filter membrane 44. Flow is in the direction of arrow B in FIG. 2B (and arrow A in FIG. 5A). This unfiltered solution 98 contains larger tissue fragments may flow to a first container 94*a*. Of course, in the embodiment where the outlet 38 is absent (or intentionally plugged), there is no need for a first container 94*a* that collects waste. Another portion 100 of the processed lipoaspirate 96 which includes cells and smaller cell clusters, however, can pass through the filter membrane 44. The fluid and the cells and cell clusters contained therein and then exit via the outlet 46 of the microfluidic tissue filtration device 30. This filtered solution containing single cells and small cell clusters may flow to a second container 94*b*. Optionally, as seen in FIG. 2B, the non-filtered solution 98 may be recirculated and pumped back through the microfluidic tissue filtration device 30. Additionally, it is possible to reverse flow through the microfluidic tissue filtration device 30 making the outlet 38 an "inlet" whereby fluid (e.g., buffer or other biological compatible fluid) is used to dislodge or remove larger tissue or cell clusters that may adhere to the filtration membrane 44. After this flushing operation, the microfluidic tissue filtration device 30 may be operated normally as described above.

Figure 2C:
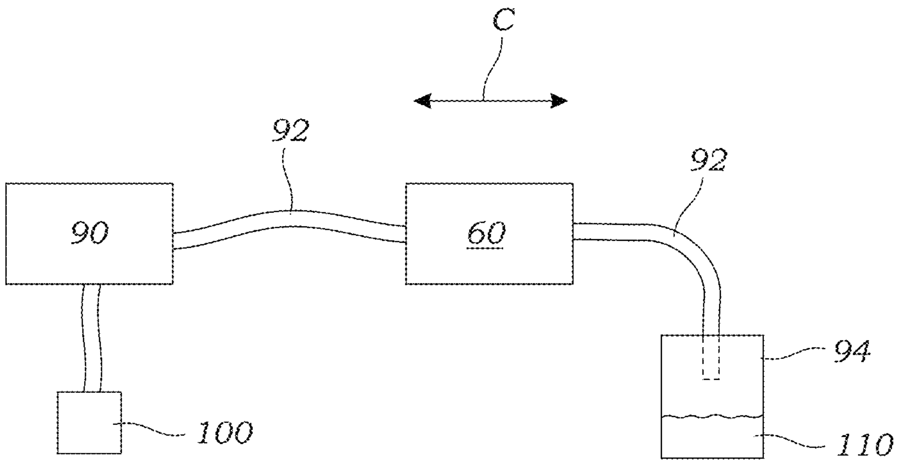
FIG. 2C schematically illustrates how a pump is used to pump lipoaspirate through the dissociation device (i.e., additional dissociation of tissue or cell clusters).

FIG. 2C illustrates the filtered lipoaspirate 100 from the microfluidic tissue filtration device 30 being pumped via pump 90 through the microfluidic dissociation device 60. FIG. 2C illustrates a pump 90 that is fluidically coupled to the microfluidic dissociation device 60 via tubing or conduit 92 and pumps the filtered lipoaspirate 100 bidirectionally through the emulsification device 10. Arrow C in FIG. 2C illustrates how the filtered lipoaspirate 4 can move in both directions through the microfluidic dissociation device 60. In the forward direction, the filtered lipoaspirate 100 may proceed through the microfluidic dissociation device 60 and into a container 94. The processed lipoaspirate 100 may then be run through the microfluidic dissociation device 60 for another "pass", for example, by reversing the flow direction of the pump 90 (e.g., using a syringe pump or the like to pull fluid (and cells) through the microfluidic dissociation device 60). This forward and reverse process may take place for a plurality of passes. FIG. 1 illustrates the final cellular suspension 110 that ultimately results from processing with the microfluidic dissociation device 60. This final cellular suspension 110 can be used directly as a therapeutic material. For example, it may be loaded into a delivery device such as a syringe and injected into mammalian tissue.

EXPERIMENTAL

Human lipoaspirate presents unique processing challenges because it is a heterogenous mixture of variously-sized tissue fragments, cells, and fatty oils that requires both micronization and emulsification. While nanofat processing has been shown to be effective, the method suffers from the fact that manual processing of nanofat is subject to user variability, which presents a challenge to generating consistent and reproducible flow rates, shear forces, and quality of the final cell suspension. Furthermore, a separate filtration step is required prior to injection. To standardize and automate the processing of lipoaspirate for clinical settings, the three device system 2 described herein (emulsification device 10, microfluidic filtration device 30, and microfluidic dissociation device 60) that can be integrated into a single platform and produce a final cell suspension 110 that can be directly injected into a mammalian subject as a therapeutic material.

The emulsification device 10 was designed to micronize and emulsify lipoaspirate 4 in a manner similar to nanofat processing using the inter-syringe method. The emulsification device 10 features, in one embodiment, two 1.5 mm diameter constriction regions 18, 20 that are separated by an abrupt expansion 22. The constrictions 18, 20 generate shear forces that break down tissue into smaller units. Based on the high viscosity of lipoaspirate 4, laminar flow is expected within the constrictions 18, 20, which will provide consistent and reliable shear forces for micronization. The rapid expansion 22 is designed to achieve turbulent mixing that will emulsify the fatty oil layer. The emulsification device 10 was fabricated by 3D printing using a biocompatible resin, with luer inlet 12 and outlet 14 ports printed on the sides of each constriction region 18, 20. 3D printing was chosen over other fabrication methods due to the ability to produce a single monolithic part 11 that could withstand high flow rates and pressures required for lipoaspirate processing, in which device clogging is commonly experienced.

Next, the microfluidic filtration device 30 captures large, mm-scale pieces of adipose tissue that remain after processing with the emulsification device 10. These large pieces of tissue could clog downstream operations such as further device processing or injection of the cellular therapeutic through small-bore needles. This replaces the standard syringe filters used for nanofat. The filtration device 30 utilizes a multi-layer design that that includes fluidic chambers or channels 36, 40 and an embedded nylon mesh filter membrane 44 (FIG. 5A). A single layer of woven Nylon mesh membrane 44 is used with pore size being either 0.5 or 1 mm. This is similar to the pore sizes used to filter nanofat prior to injection. Due to the large volume of lipoaspirate 4 samples, the surface area of the membrane 44 was increased by >10-fold, and added a grid support layer/structure 52 underneath to prevent collapse. Devices 30 were fabricated by ALine, Inc. using a commercial laminate approach, where fluidic channels 36, 40 and openings for membranes, lures 34, 38, and hose barbs 46 were micromachined into acrylic layers 32_a-f_ using a $CO_2$ laser. Nylon mesh membranes 44 with 500 and 1,000 μm pore sizes were laser cut to appropriate size. Device layers 32_a-f,_ nylon mesh membranes 44, luers 34, 38, and hose barbs 46 were then assembled, bonded using adhesive, and pressure laminated to form a single monolithic device (FIG. 5B). Luer outlet 38 may be omitted in some embodiments.

Finally, the microfluidic dissociation device 60 (FIG. 1, FIG. 2C, FIGS. 6A, 6B) further breaks-down remaining aggregates and enhance stem/progenitor cell activity. Reducing the size of aggregates helps prevent needle clogs during injection of the final cellular therapeutic material 110, as well as ensure injected tissue fragments are small enough to survive without being vascularized. The dissociation device 60 design was modified from previous work, in which the goal was to generate single cells solid tissue samples. Since reaching the single cell level is not required for therapeutic applications of SVF, the dimensions of the features of the channels 64, 66, 70, 72 were increased in terms of width and height. Specifically, the dimensions of the dissociation device 60 are 3000, 1500, and 750 μm in width (measured at the constrictions 74) for the three (3) different stages. The height was 750 μm in each stage. Devices 60 were 3D printed using a biocompatible resin. The branching network of channels 64, 66, 70, 72 in this device 60, as well as the luer inlet port 62 and luer outlet port 68, were printed as a single part in order to better withstand the high flow rates and pressures experienced during device operation. FIG. 6A illustrates a perspective view of the complete dissociation device 60. For all devices 10, 30, 60 used in the experiments described herein, a pump 90 (e.g., syringe pump) was used to pass lipoaspirate 4 through the respective device 10, 30, 60. For some devices like the emulsification device 10, the lipoaspirate 4 was passed back-and-forth a plurality of times (e.g., 10, 20, 30, 40, or more times) as seen in FIG. 2A. The tissue dissociation device 60 may also involve back-and-forth movement of the lipoaspirate 4 which can be done using a pump 90 (e.g., syringe pump) as seen in FIG. 2C. For the microfluidic filter device 30, the emulsified lipoaspirate 4 is, in one embodiment, pumped in a single direction through the microfluidic filter device 30 where the filtrate which contains the filtered lipoaspirate 4 is collected or passed to the dissociation device 60. The effluent from the outlet 38, if present, may be discarded as waste as illustrated in FIG. 2B. Alternatively, the effluent from the outlet 38, when present, may be recycled back to the inlet 34 as illustrated by the dashed line of FIG. 2B. Different types of pumps 90 may be used including not only syringe pumps but also peristaltic pumps.

While FIGS. 2A-2C separately illustrate the three operations of emulsification, filtering, and dissociation it should be appreciated that the three operations can be linked together with multiple pumps 90, tubing 92 or conduits, and valves such that the emulsified lipoaspirate 96 that is produced by emulsification device 10 is then pumped to the microfluidic filtration device 30 for filtration. The filtrate 100 from the microfluidic filtration device 30 can then be pumped to the microfluidic dissociation device 60 for processing. In this regard, a complete, integrated system 2 such as that illustrated in FIG. 1 is formed in which the user supplies the raw lipoaspirate 4 to the system 2 which then outputs the final cellular suspension 110 for use.

Emulsification Device Optimization

Figure 7A:
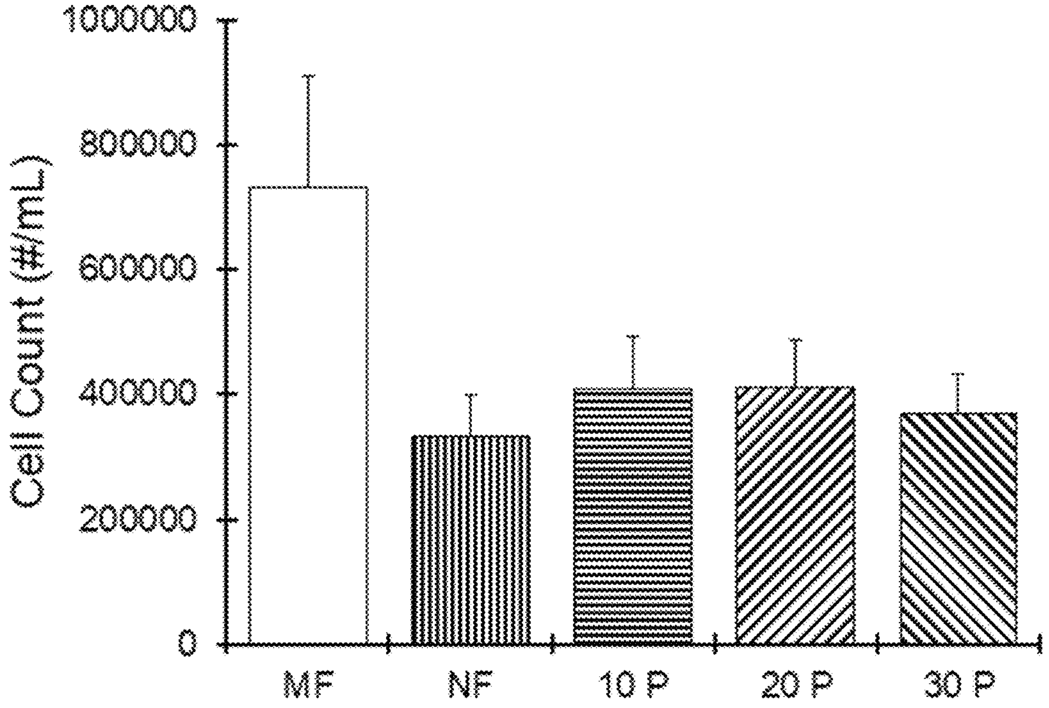
FIGS. 7A-7C illustrate emulsification device results. Healthy human LA (N=5) was mechanically processed using 2 syringes (nanofat, NF) or the emulsification device for 10, 20, or 30 passes (10 P, 20 P, 30 P). Unprocessed LA is indicated as macrofat (MF). All samples were digested with collagenase prior to cell analysis. Nucleated cell counts decreased by half for nanofat and all device-processed conditions (FIG. 7A). Nucleated cell viability remained at ~90% for all conditions (FIG. 7B). Mechanical processing enriched all cell types of interest, often by 2- to 3-fold compared to unprocessed MF, with the emulsification device providing similar or improved results compared to NF (FIG. 7C). Error bars represent standard errors from at least three independent experiments. * indicates $p<0.05$ and ** indicates $p<0.01$ relative to MF.
Figure 7B:
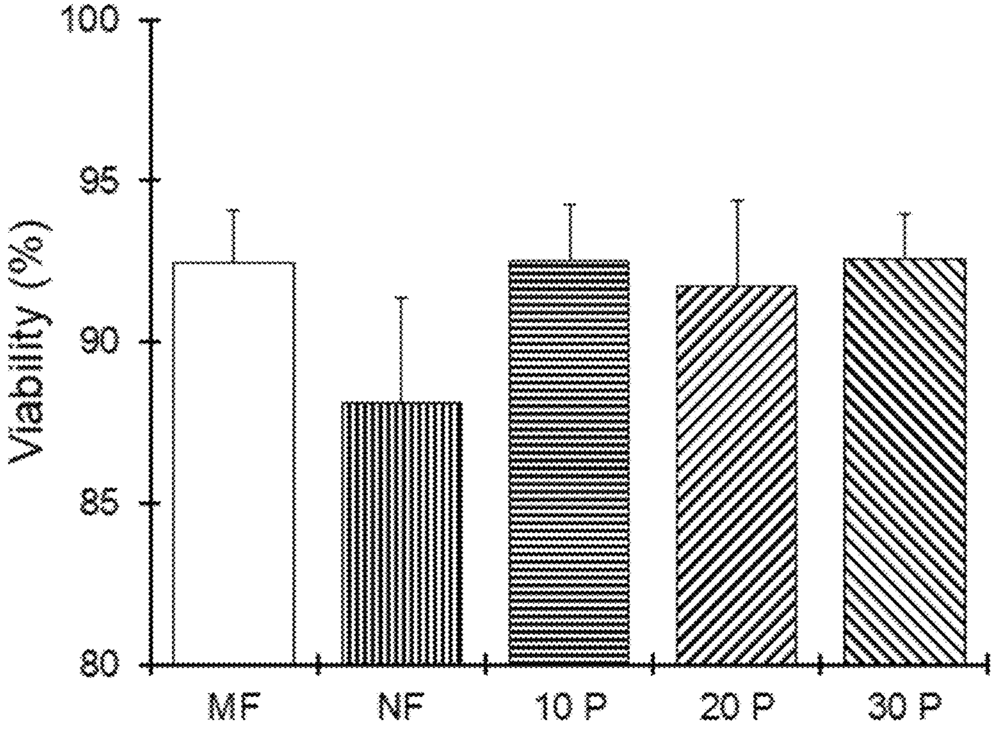

Performance of the emulsification device 10 was evaluated using human lipoaspirate (LA) samples obtained both healthy and diabetic patients using standard tumescent, vacuum-assisted liposuction. LA was washed with phosphate-buffered saline (PBS) and sub-divided into separate portions. One portion was not mechanically processed, termed macrofat (MF). Another portion was processed into nanofat by manually passing 30 times between two connected syringes, as originally described by Tonnard et. al. Remaining samples were processed with the emulsification device for 10, 20, or 30 passes using a syringe pump 90 set to a flowrate of 20 mL/s, approximately the same flowrate used to manually produce nanofat. All samples were then digested with collagenase to isolate SVF, as previously described. Nucleated cell counts and viability were determined using an automated, dual-fluorescence cell counter. For healthy patients (N=5), macrofat samples yielded the highest cell counts at approximately 700,000 cells/mL LA (FIG. 7A). Nanofat and all emulsification device conditions had lower cell counts by nearly half. Decreased cell counts were likely due to destruction of fragile cells by shear forces, which has previously been observed for adipocytes during nanofat processing. However, viability was found to be similar at ~90% for all conditions (FIG. 7B). This suggests that the cells that were lost during nanofat or device processing were reduced to debris and removed during subsequent washing steps or could not be recognized as a cell by automated cell counter.

Next, flow cytometry was performed and the fluorescent probe panel listed in Table 1 (below) to identify the stem and progenitor cell subsets listed in Table 2 (below).

TABLE 1

| Assay | Probe |
|---|---|
| CD34 | Anti-CD34 Ab (clone 561)-BV421 |
| CD45 | Anti-CD45 Ab (clone 2D1)-BV510 |
| SSEA-3 | Anti-SSEA-3 Ab (clone MC-631)-FITC |
| CD26 | Anti-CD26 Ab (clone BA5b)-PE |
| CD31 | Anti-CD31 Ab (clone WM59)-PE/Cy7 |
| CD55 | Anti-CD55 Ab (clone JS11)-APC |
| CD13 | Anti-CD13 Ab (clone WM15)-APC/Cy7 |
| Viability | 7-AAD |

TABLE 2

| Cell type | Markers | Significance |
|---|---|---|
| CD34+ | CD34+ | Common marker for multipotentiality |
| Mesenchymal Stem Cells (MSCs) | CD45−, CD31−, CD34+ | Key in regenerative wound healing |
| Endothelial Progenitor Cells (EPCs) | CD45−, CD31+, CD34+ | Vascularization of healing tissues |
| Multilineage Differentiating Stress-Enduring (Muse) | CD45−, CD31−, CD34+, SSEA-3+, CD13+ | Nontumorigenic, pluripotent, stress tolerant stem cells |
| DPP4+/CD55+ | CD45−, CD31−, CD34+, CD26+, CD55+ | Improved wound healing in diabetic models |

Figure 10:
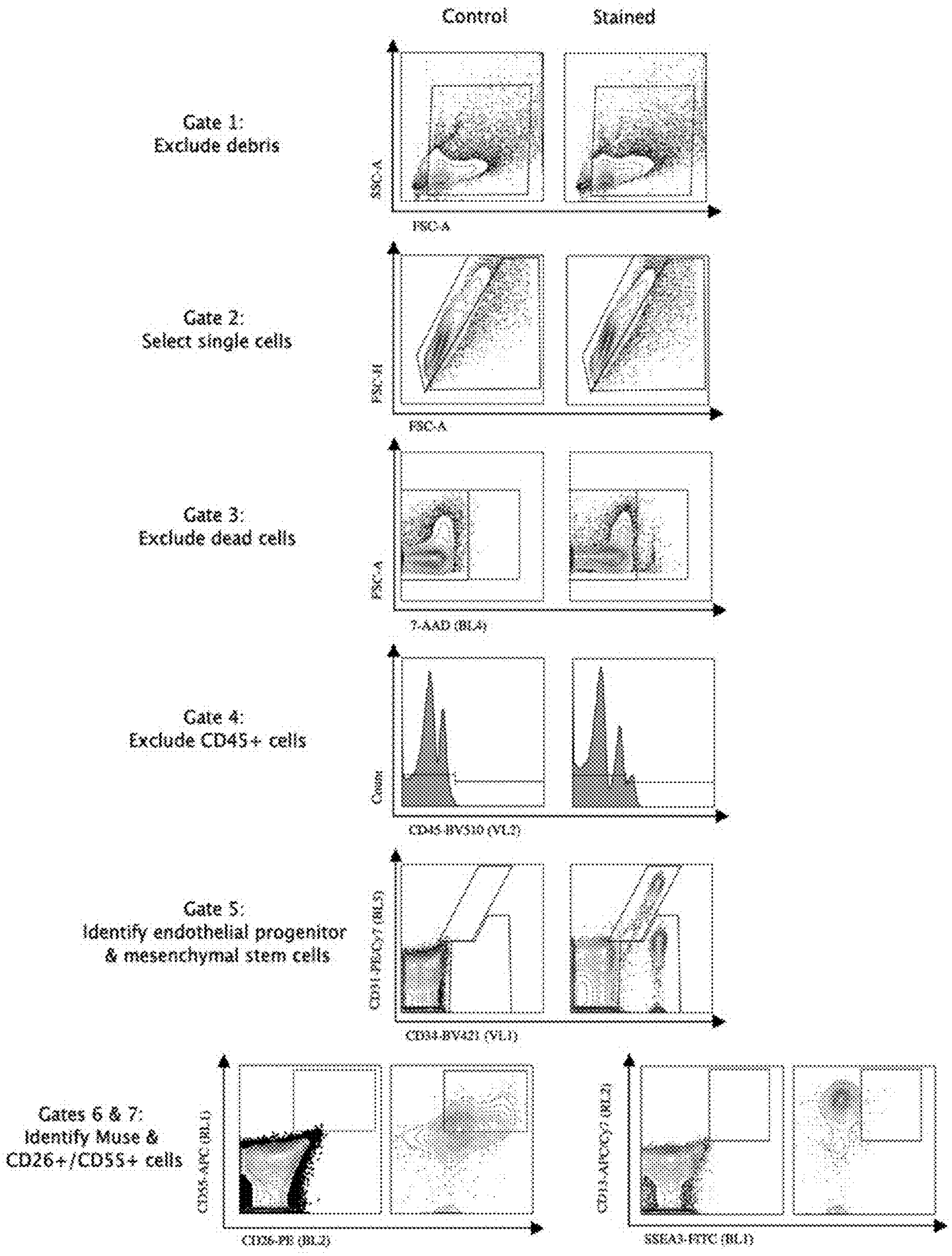
FIG. 10 illustrates the flow cytometry gating scheme. Following collagenase digestion, cell suspensions were stained with fluorescent probes listed in Table 1 and analyzed using flow cytometry. Acquired data was compensated and assessed using a sequential gating scheme. Gate 1, based on FSC-A vs. SSC-A, was used to exclude debris near the origin. Gate 2 was then used to select single cells based on FSC-A vs. FSC-H. Gate 3 was used to exclude dead cells based on positive 7-AAD signal. Gate 4 was applied to the live cell subset to exclude hematopoietic cells based on positive CD45−BV510 signal. Gate 5 was applied to the CD45− cell subset to identify endothelial progenitor cells based on positive CD34−BV421 and CD31−PE/Cy7 signals, and to identify mesenchymal stem cells (MSCs) based on positive CD34−BV421 and negative CD31−PE/Cy7 signals. Gate 6 was applied to the CD34+, CD31− MSC subset to identify CD26+/CD55+ cells based on positive CD26−PE and CD55−APC signals. Gate 7 was applied to the CD34+, CD31− MSC subset as well, in order to identify multilineage differentiating stress enduring (Muse) cells based on positive SSEA3-FITC and CD13−APC/Cy7 signals. Appropriate isotype controls were used to assess nonspecific background staining, and appropriate fluorescence minus one (FMO) controls were used to determine positivity and set gates.

The sequential gating scheme is illustrated in FIG. 10. CD34 is of interest because it is a known stem cell marker, and higher percentages of CD34+ cells in SVF has been linked to improved fat graft survival. MSCs are essential in wound healing due to their differentiation potential, anti-inflammation characteristics, and paracrine and immunomodulatory functions, while endothelial progenitor cells have been implicated as a key cell type in revascularization due to angiogenic and paracrine effects. Muse and DPP4+/CD55+ cells are both subtypes of MSCs that are of particular interest in regenerative medicine. Muse cells are known to be pluripotent, nontumorogenic, and extremely stress tolerant stem cells. Both Muse and DPP4+/CD55+ cells have also been shown to improve wound healing in diabetic murine models.

Figure 7C:
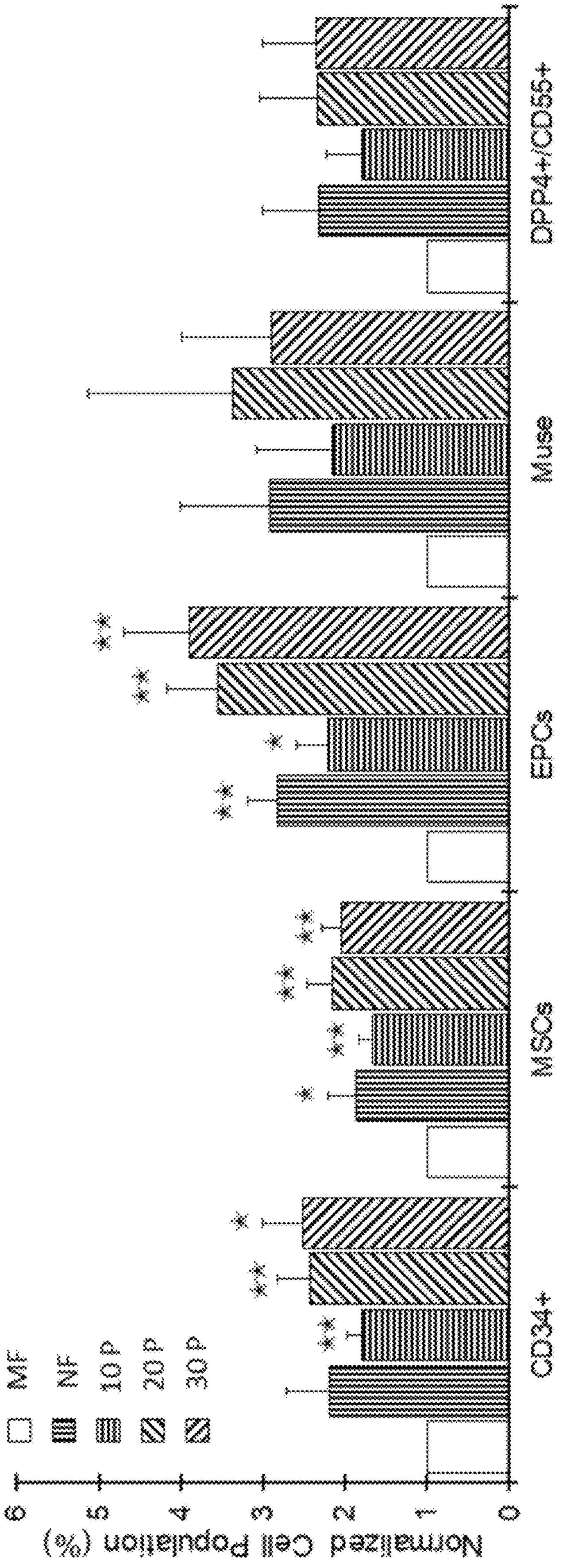

The various stem/progenitor populations measured for healthy patients are shown in FIG. 7C. Results were normalized to macrofat, as relative numbers within SVF have been shown to vary widely across different patients and anatomical locations of adipose tissue harvest. Nanofat processing enriched all cell populations by 2- to 3-fold, as shown previously for all but the DPP4+/CD55+ case. Emulsification device processing also enriched all cell populations, which increased between 10 and 20 passes, however, 30 passes did not provide significant increases. Overall, nanofat and emulsification device processing provided comparable enrichment of CD34+ cells (~2.5-fold), MSCs (~2-fold), Muse cells (~3-fold), and DPP4+/CD55+ cells (~2.5-fold). EPCs were slightly higher for the emulsification device 10 (~4-fold) relative to nanofat (~3-fold), but this difference was not statistically significant.

Figure 11A:
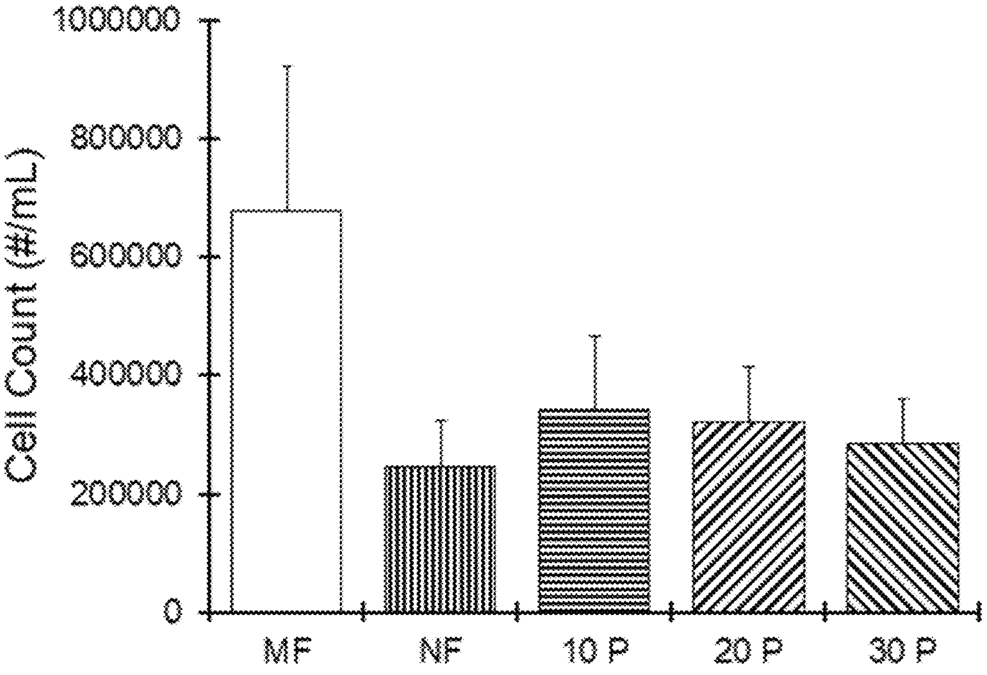
FIGS. 11A-11C illustrate emulsification device results for diabetic patients. Diabetic human LA (N=4) was mechanically processed using 2 syringes (nanofat, NF) or the emulsification device for 10, 20, or 30 passes (10 P, 20 P, 30 P, respectively). Unprocessed LA is indicated as macrofat (MF). All samples were digested with collagenase prior to cell analysis. Results for (FIG. 11A) nucleated cell counts, (FIG. 11B) viability, and (FIG. 11C) normalized cell populations closely followed trends shown in FIGS. 7A-7C for healthy lipoaspirate samples.
Figure 11B:
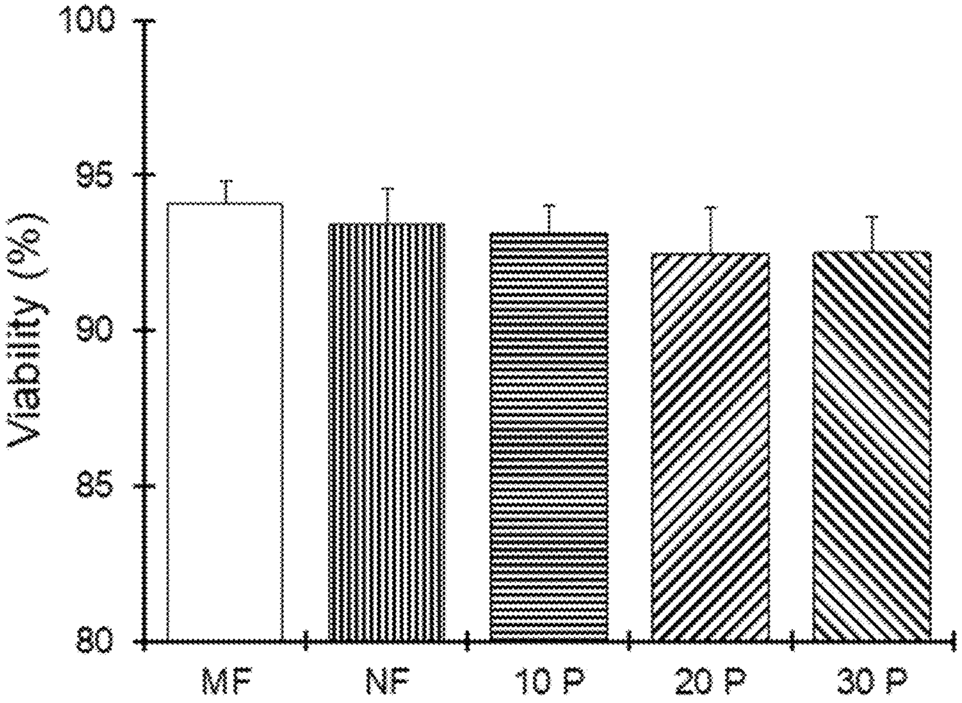
Figure 11C:
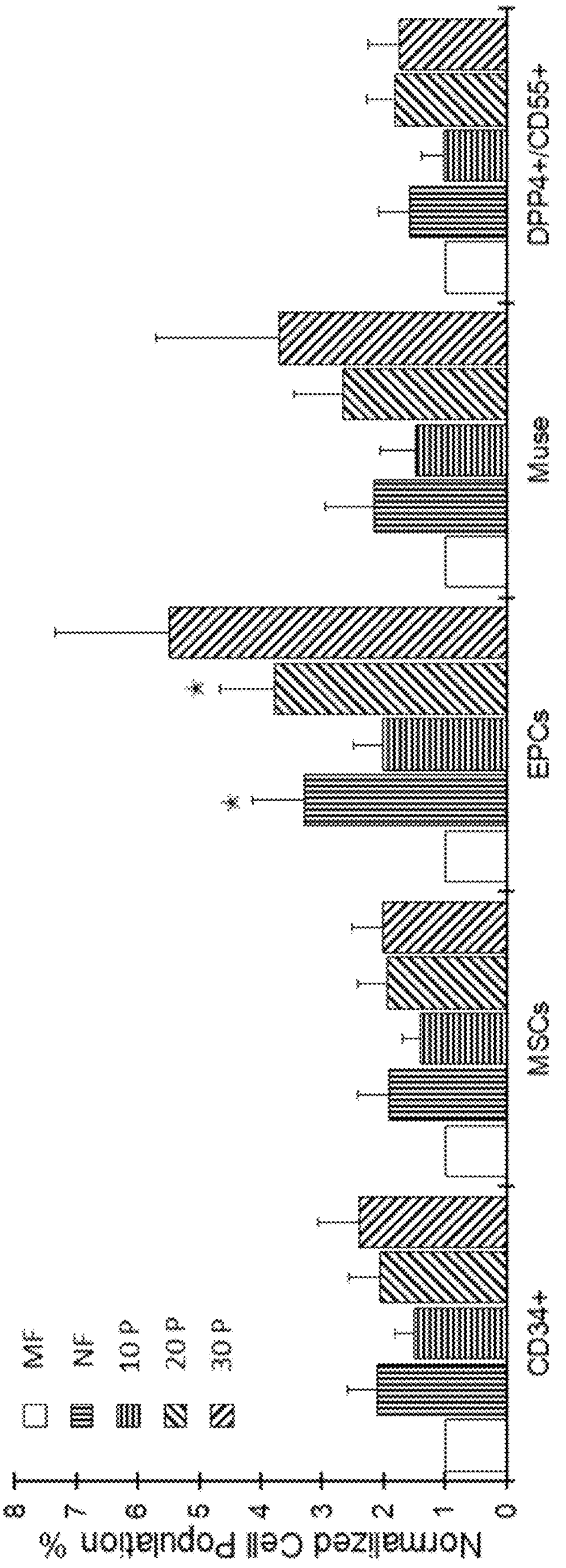

For a cohort of diabetic patients (N=4), similar trends in cell count, viability, and stem/progenitor cell enrichment were observed for nanofat and emulsification device 10 processing conditions (see FIGS. 11A-11C). Specifically, EPCs were again higher for the emulsification device 10 in comparison to nanofat, but still not significant. Enrichment of these stem/progenitor populations is particularly encouraging in the context of diabetes, as wound healing and neovascularization are well known to be significantly impaired. For adipose tissue specifically, diabetes has been shown to deplete key subpopulations of ADSCs, resulting in impaired angiogenic potential. This could ultimately limit their usefulness in autologous therapies for diabetics, highlighting the need for methods that can successfully enhance these depleted populations in an effort to improve efficacy.

Filter Device Optimization

Figure 8A:
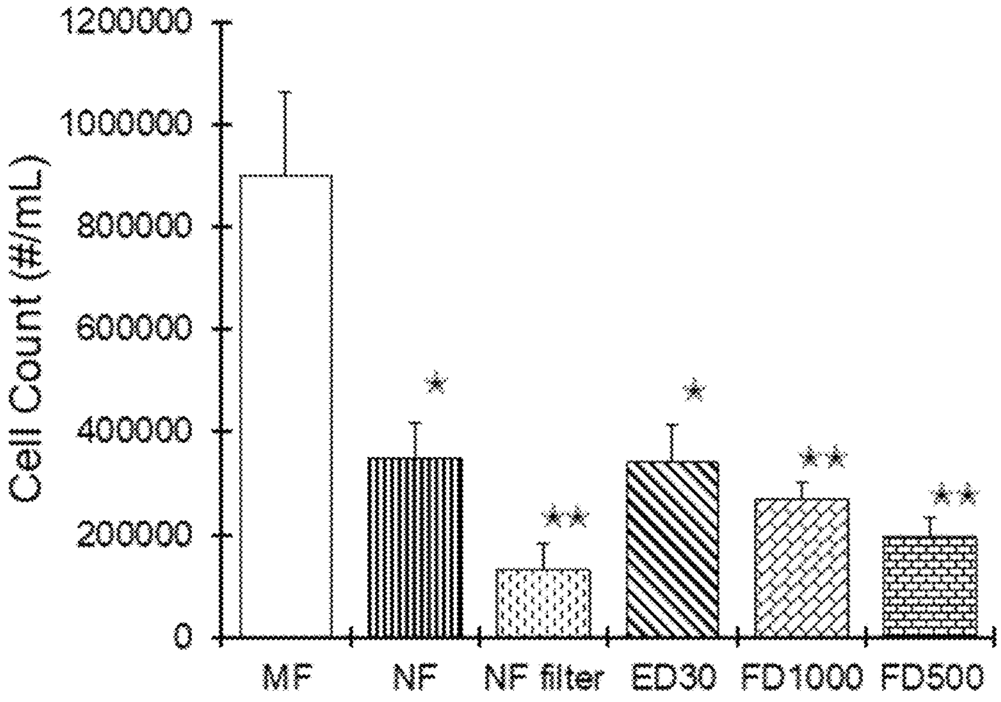
FIGS. 8A-8C illustrate lipoaspirate microfluidic filter device results. Healthy human LA (N=4) was mechanically processed using 2 syringes (nanofat, NF) or the emulsification device for 30 passes (ED30). NF was also manually filtered using a 1,000 μm mesh cloth (NF filter), while ED30 samples were filtered using the microfluidic filter device (FD) with 1,000 or 500 μm pores (FD1000 and FD500, respectively). Unprocessed LA is indicated as macrofat (MF). All samples were digested with collagenase prior to cell analysis. Nucleated cell counts decreased by over half for NF and ED30 processed samples, and further decreased with filtering, most notably for the NF mesh filtered condition (FIG. 8A). Nucleated cell viability remained >90% for all conditions (FIG. 8B). ED30 followed by LA filter device enriched all cell types of interest, except for Muse and DPP4+/CD55+ cells, with improved results compared to MF and NF filtered conditions (FIG. 8C). Error bars represent standard errors from at least three independent experiments. * indicates $p<0.05$ and ** indicates $p<0.01$ relative to MF. # indicates $p<0.05$ relative to NF filtered and ## indicates $p<0.01$ relative to NF.
Figure 8B:
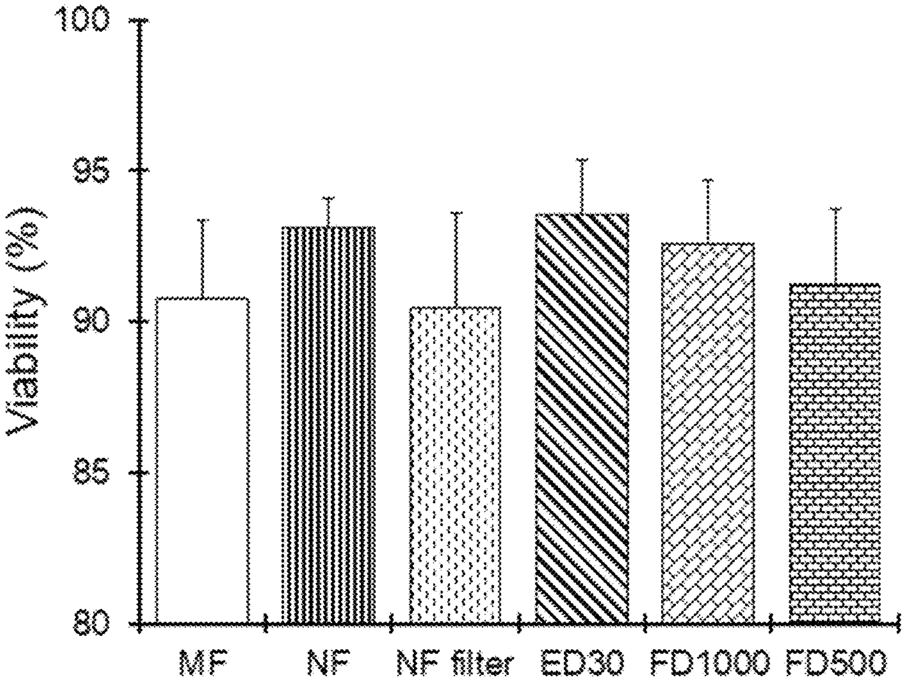

Next, microfluidic filter devices 30 were tested on lipoaspirate 96 that was first processed using the emulsification device 10 for 30 passes. This is intended to replace the manually filtering step that is needed prior to injection of nanofat. Microfluidic filter devices 30 were evaluated containing either 500 or 1,000 μm nylon mesh membranes 44. For comparison, nanofat was also tested after passing through a 1,000 μm mesh cloth. After processing, samples were digested with collagenase and tested for cell count, viability, and stem/progenitor content as in the previous section. Since normal and diabetic samples responded similarly to nanofat and emulsification device processing, only healthy fat was evaluated for these tests (N=4). Total cell counts for macrofat, nanofat, and emulsification device conditions were similar to the tests. Total cell number was $9.0\times10^5$ cells/mL for macrofat, and decreased to $\sim3.5\times10^5$ cells/mL for both nanofat and the emulsification device 10 (FIG. 8A), consistent with the initial experiments (FIG. 7A). Manually filtering nanofat drastically reduced cell count to $1.3\times10^5$ cells/mL. This indicates that most of the nanofat sample would be lost during filtering and not ultimately be used as an injectable therapeutic. The filter device 30 better preserved cell recovery in the emulsification device 10 sample, resulting in recovery of 2.7 and $2.0\times10^5$ cells/mL for the 1,000 and 500 μm mesh membranes 44, respectively. The 500 μm membrane 44 likely removed larger tissue fragments in a similar manner to the manual mesh filter. It is notable that the filter device 30 with 1,000 μm membrane 44 utilized the same pore size as the manual filter, but allowed 2-fold more cells to pass through. It is unclear whether this was related entirely to the filter step, or whether differences in upstream processing, emulsification device versus nanofat, were also at play. It is believed that the microfluidic filter device 30 was at least primarily responsible for improved performance, which could have resulted from a larger membrane 44 surface area or smaller device hold-up volume. Moreover, the microfluidic filter device 30 may have promoted extrusion, or even direct dissociation, of most of the large tissue fragments. Cell viability remained high, in excess of 90%, for all conditions (FIG. 8B).

Figure 8C:
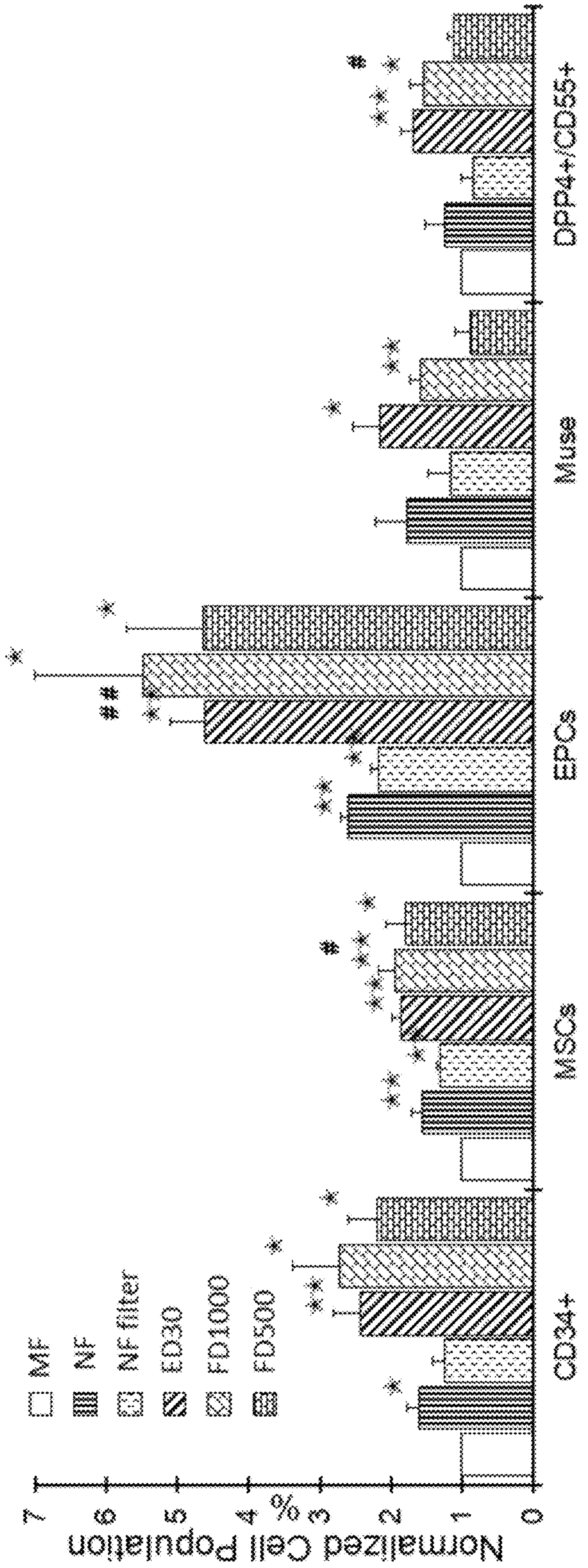

Flow cytometry analysis was then performed to determine whether filtering mm-scale aggregates that were more difficult to dissociate would have an adverse effect on the recovery of stem or progenitor cell populations. For this patient cohort, the emulsification device 10 produced a substantially higher proportion of CD34+ cells and EPCs compared to nanofat (FIG. 8C). Specifically, there were ~1.5-fold more CD34+ cells and >2-fold more EPCs, with the EPC difference being significant. After manually filtering nanofat, a decrease in all stem/progenitor populations was observed (FIG. 8C). In fact, population percentages for filtered nanofat were reduced back to macrofat levels for all but MSCs and EPCs. It should be noted that the lower relative number of stem/progenitor cells obtained upon manual filtering of nanofat exacerbates the loss to total cells in FIG. 8A, resulting in a net loss ranging from 3- to 4-fold for all stem/progenitor populations. Conversely, the filter device 30 generally retained similar relative numbers of CD34+ cells, MSCs, and EPCs compared to the emulsification device 10 without filtering. This was true for both 500 and 1,000 μm pore sizes. Muse and DPP4+/CD55+ cell populations, however, were reduced by the filter device 30, in a dose-dependent manner with pore size. This finding suggests that a significant portion of the Muse and DPP4+/CD55+ cell populations reside within the largest tissue fragments that remain after nanofat or emulsification device processing. Compared to NF filtered samples, device 30 filtered samples yielded ~2-fold more CD34+ cells, ~1.5-fold more MSCs, and 2 to 2.5-fold more EPCs. These results show that the microfluidic filter devices 30 are more effective at dissociating cell aggregates containing these stem/progenitor populations to a degree that they are able to pass through the filters 44 and be recovered. The 1,000 μm pore microfluidic filter device 30 yielded higher Muse and DPP4+/CD55+ populations than both the 500 pore device and NF filtered conditions. Based on this preliminary data, the 1,000 μm microfluidic filter device 30 generally outperforms the 500 μm device 30, maintains the stem/progenitor populations most similar to a comparable unfiltered counterpart, and was used for integration with the microfluidic dissociation device 60.

Microfluidic Dissociation Device Optimization

Figure 9A:
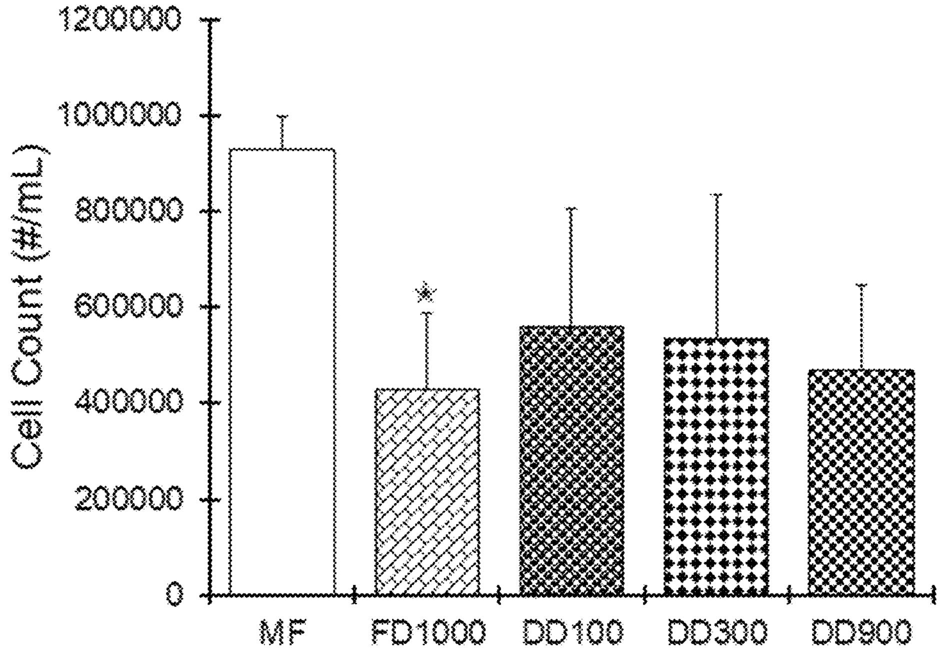
FIGS. 9A-9C illustrate lipoaspirate dissociation device results. Healthy human LA (N=3) was mechanically processed using the emulsification device for 30 passes and the LA filter device with 1,000 μm membrane (FD1000). Samples were then processed using the LA dissociation device (DD) for 20 passes at 100, 300, or 900 mL/min flow rate (DD100, DD300, DD900, respectively). Unprocessed LA is indicated as macrofat (MF). All samples were digested with collagenase prior to cell analysis. Nucleated cell counts decreased by ~half for all device processed samples compared to unprocessed MF (FIG. 9A). Nucleated cell viability remained at ~90% for all conditions (FIG. 9B). Dissociation device processing increased CD34+ and EPC populations modestly in a dose-dependent manner, while MSC and DPP4+/CD55+ populations were unaffected and Muse cells decreased with flow rate (FIG. 9C). Error bars represent standard errors from at least three independent experiments. * indicates $p<0.05$ and ** indicates $p<0.01$ relative to MF. # indicates $p<0.05$ relative to FD1000.
Figure 9B:
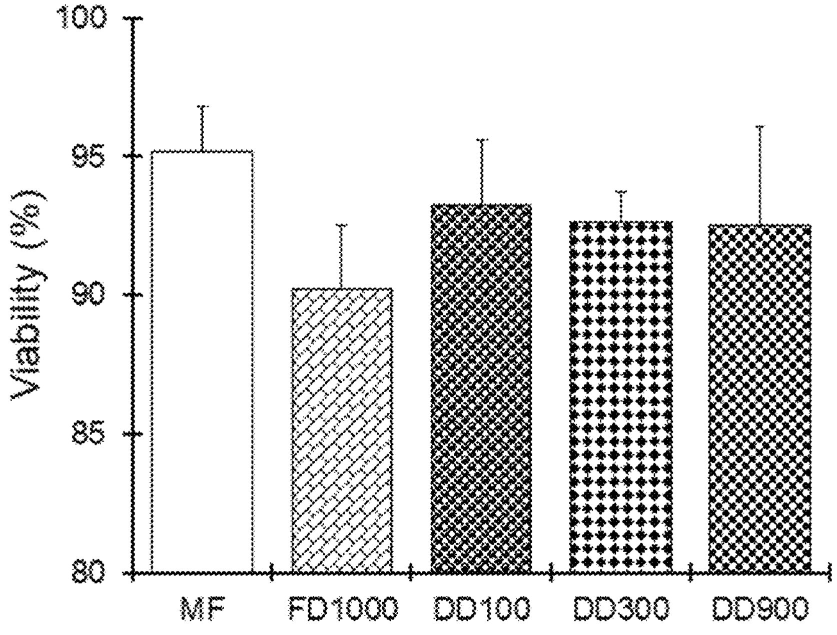

Next, the microfluidic dissociation device 60 was tested using lipoaspirate 100 from healthy patients (N=4) that was first processed using the emulsification device 10 for 30 passes followed by the 1,000 μm microfluidic filter device 30. Samples were then processed using 20 passes through the microfluidic dissociation device 60 at a flow rate of 100, 300, or 900 mL/min. This was intended to further break down aggregates and enrich key stem and progenitor cell populations. After processing, samples were digested with collagenase and quantified for cell count, viability, and stem/progenitor content as in the previous section. Total cell counts for macrofat were $9.3\times10^5$ cells/mL, and decreased by a factor of ~2 for all device 60 conditions (FIG. 9A), similar to previous experiments (FIGS. 7A and 8A). All dissociation device 60 conditions generated comparable total cell numbers, and cell viability remained at greater than 90% for all conditions (FIG. 9B), suggesting that the majority of cells can withstand the enhanced shear forces generated during dissociation.

Figure 9C:
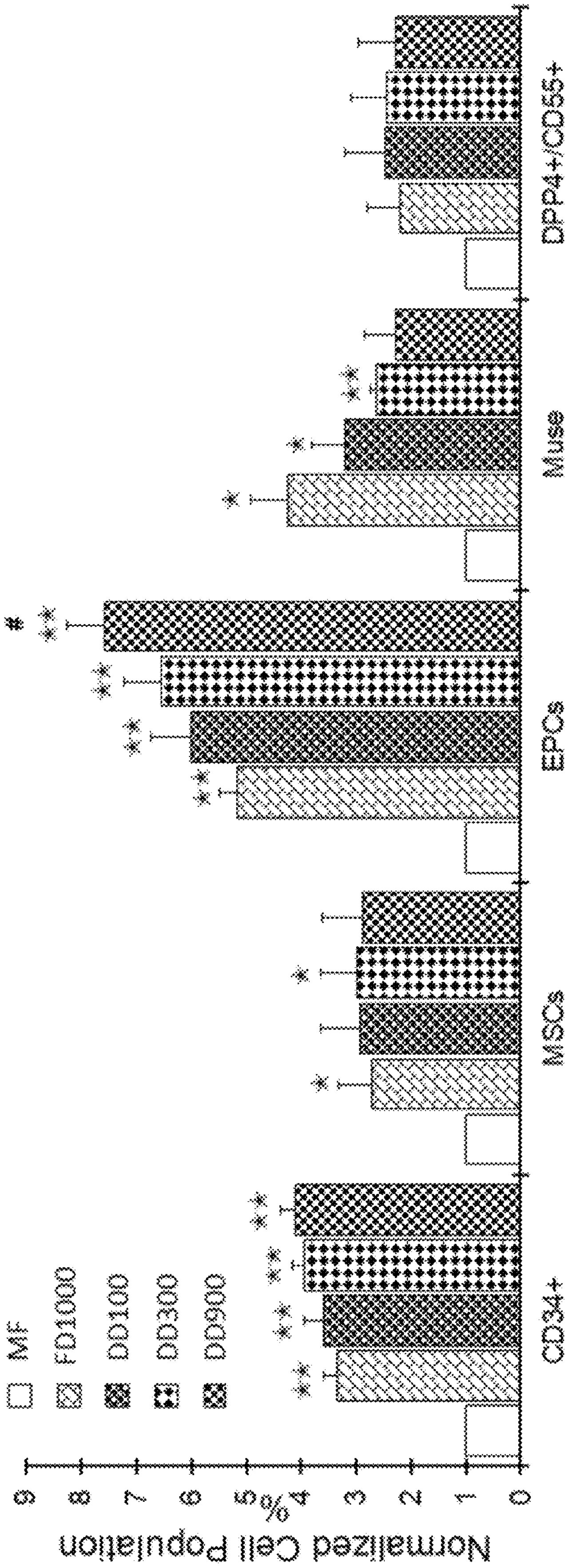

Flow cytometry analysis was then performed to determine the effect of dissociation device processing has on key stem and progenitor cell populations. Dissociation device processing resulted in a dose dependent increase in CD34+ cells with flow rate (FIG. 9C), from ~3.3-fold higher than macro fat without dissociation to ~4-fold higher than macrofat for the 900 mL/min condition. However, the differences amongst device 60 conditions were not significant. The MSC population was not affected by dissociation device treatment, remaining at 3-fold higher than macrofat. EPCs, however, increased in a dose dependent manner from ~5-fold for S30+1000 to over 7.5-fold for the 900 mL/min condition. Interestingly, Muse cells decreased as dissociation processing increased, suggesting that Muse cells may be susceptible to damage from high mechanical shear forces. The most aggressive mechanical 900 mL/min dissociation device treatment still yielded over 2-fold increase in Muse population compared to macrofat, however. DPP4+/CD55+ cell populations were unaffected by dissociation device processing, remaining at ~2.5-fold higher than macrofat.

Gene Expression in Response to Device Processing

Figure 12A:
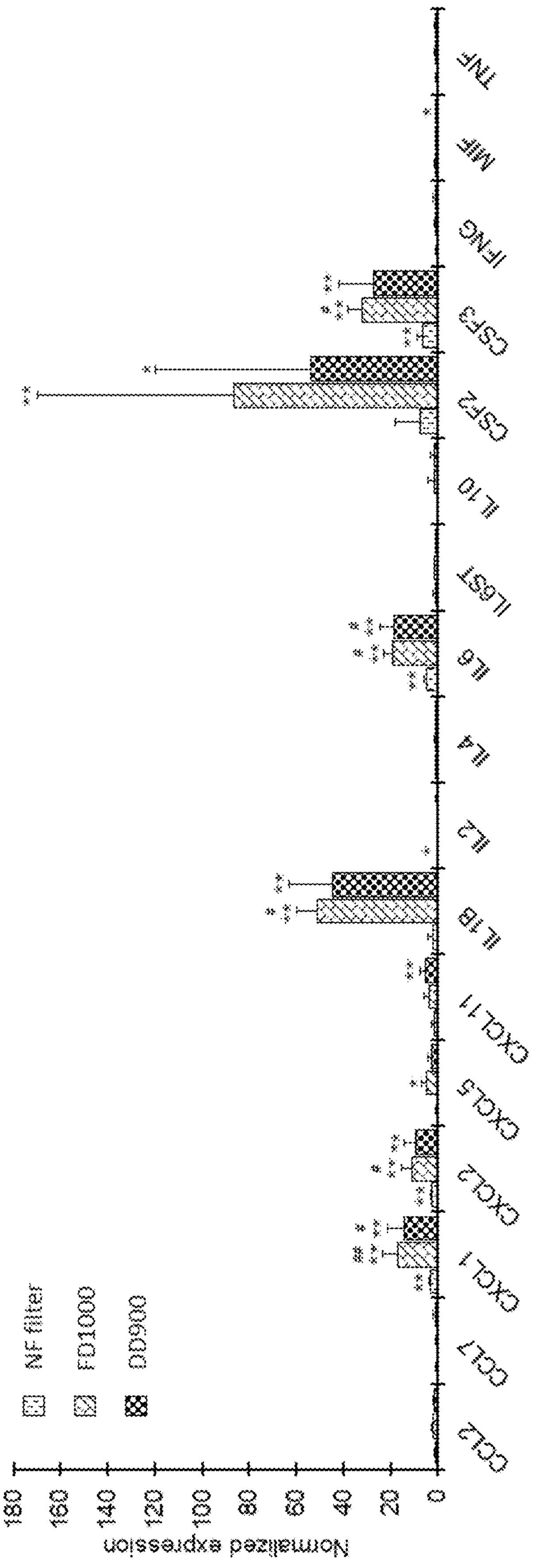
FIGS. 12A-12E illustrate reverse transcription-quantitative polymerase chain reaction (RT-qPCR) results for the filtration device and dissociation device. Healthy human LA (N=4) was mechanically processed using two (2) syringes and manually filtered using a 1,000 μm mesh cloth (NF filter) or the emulsification device for 30 passes followed by only the 1,000 μm pore filtration device (FD1000) or both the 1,000 μm pore filtration device and the LA dissociation device at 900 mL/min flowrate (DD900). All samples were collected and cultured for 24 hours at 37° C. in order to allow time for transcriptional changes to occur. Bulk RNA was the extracted and quantified by RT-qPCR. Results for each sample were normalized to expression of reference gene RPLP0. NF filter and device processed samples were then normalized to MF. Results for cytokine (FIG. 12A), growth factor (FIG. 12B), ECM-related (FIG. 12C), integrin (FIG. 12D), and other wound healing related genes suggest that device processing can significantly alter expression of key genes involved in wound healing and angiogenesis. Error bars represent standard errors from at least three independent experiments. * indicates $p<0.05$ and ** indicates $p<0.01$ relative to MF. # indicates $p<0.05$ relative to NF filter and ## indicates $p<0.01$ relative to NF filter.
Figure 12B:
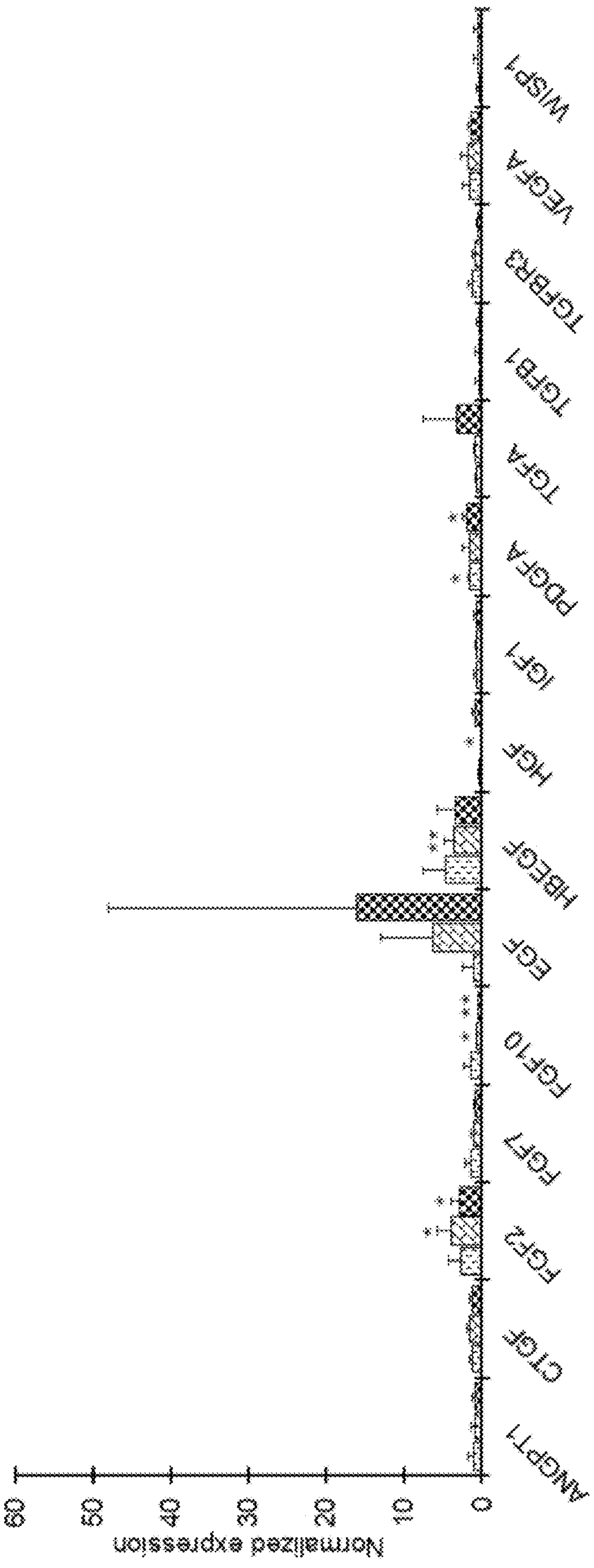
Figure 12C:
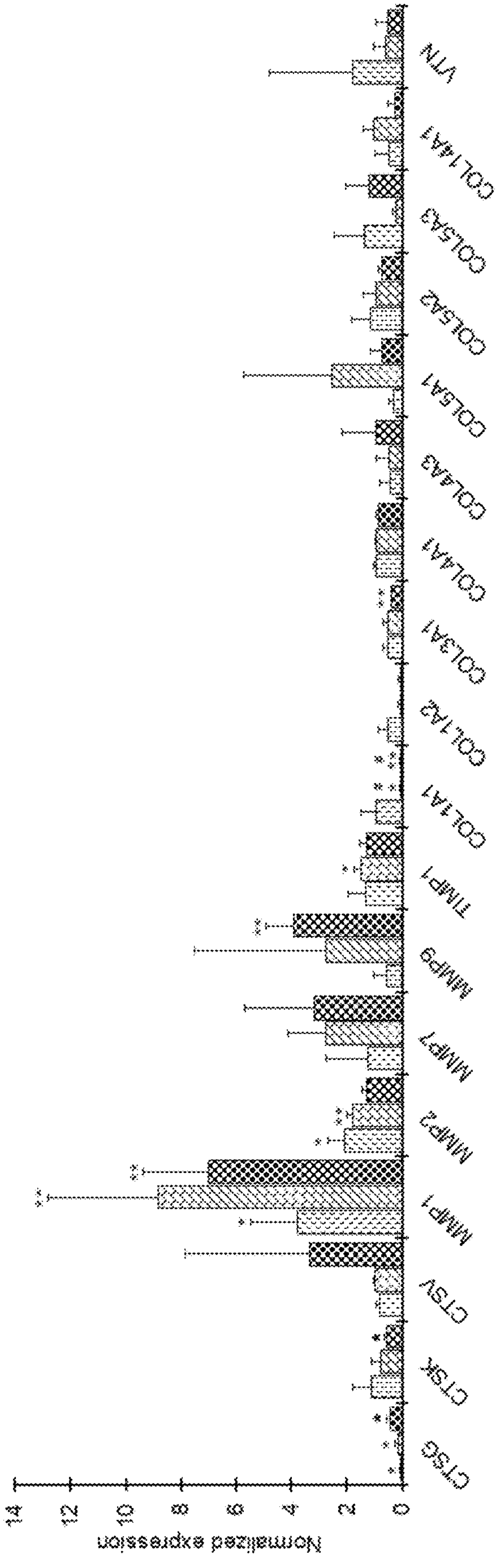
Figure 12D:
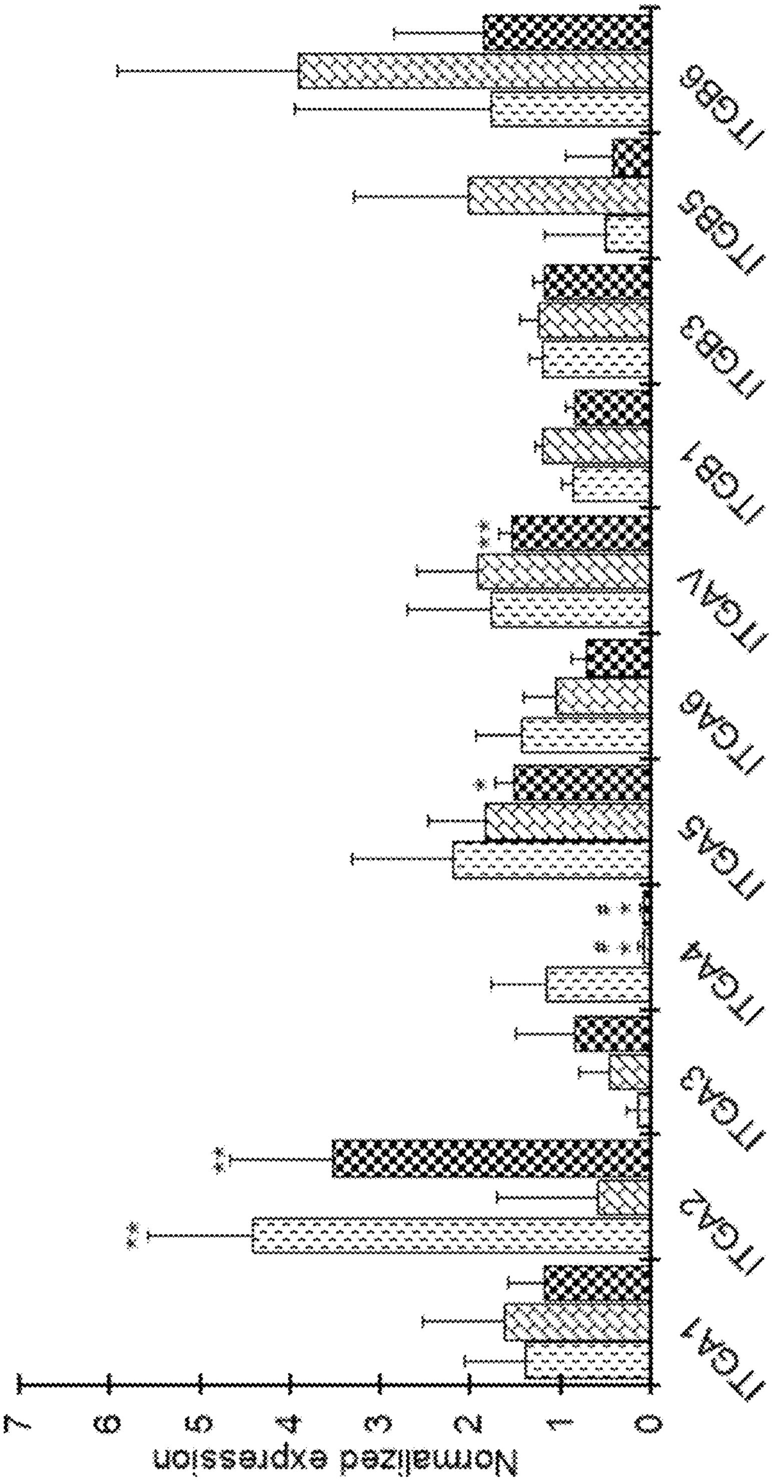
Figure 12E:
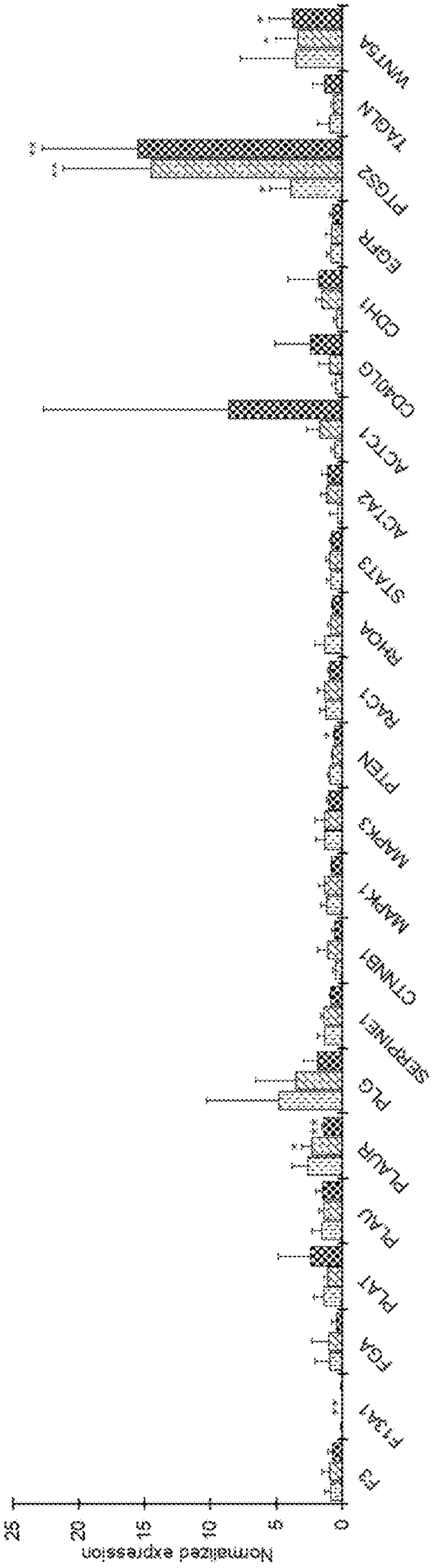

To investigate the effect of mechanical processing with the devices 10, 20, 60, the expression of wound healing-related genes was assessed by real-time quantitative polymerase chain reaction (RT-qPCR). Specifically, RT-qPCR was used to test macrofat (MF), nanofat (NF) with filtering (NF filter), emulsified lipoaspirate processed with the emulsification device 10 (referred to as ED (30 passes)) plus filtration using the microfluidic filtration device 30 (referred to herein as FD) (1000 μm), and ED30/FD1000 plus+which was run through the microfluidic dissociation device 60 at 900 mL/min (referred herein as DD900). Samples were collected and cultured for 24 hours at 37° C. in order to allow time for transcriptional changes to occur. Bulk RNA was then extracted and a gene panel was quantified by RT-qPCR. Results for each sample were then normalized to expression of reference gene RPLP0. NF filter and device-processed samples were then normalized to MF. Results are presented in FIGS. 12A-12E. Numerous genes involved in wound healing and angiogenesis were upregulated in both NF filter and device-processed samples. CSF3 (G-CSF) expression was highly upregulated in all processed conditions, by 6-fold for NF-filter and ~30-fold for both device conditions (FIG. 12A). These results are promising, as G-CSF is known to improve wound healing. Similar trends were seen for CXCL1 and CXCL2, two pro-angiogenic chemokines involved in wound healing, where all processed conditions were upregulated, with FD1000 significantly upregulated compared to NF filter (FIG. 12A). The MMP family, known for playing a pivotal role in re-epithelialization in both acute and chronic wounds, were also generally upregulated. Most promisingly, MMP1 was significantly upregulated for all processed conditions (4-fold for NF filter, 9-fold for 1000FD, 7-fold for 900DD) (FIG. 12C). FGF2 and PDGFA, two important growth factors for promoting angiogenesis and the migration of fibroblasts, were also significantly upregulated (FIG. 12B). For FGF2, there was a 3-4-fold upregulation for all processed conditions, although significant only for the device processed samples (FIG. 12B). PDGFA was modestly upregulated by 1.5- to 2-fold for all processed conditions, although only significantly for NF filter and 900DD. ITGAV (FIG. 12D), an integrin involved in angiogenesis, was upregulated 1.5 to 2-fold for all processed conditions, significantly for the 900DD condition. PTGS2 (FIG. 12E), another gene known to be upregulated in cells mechanical shear forces, was significantly upregulated in for all processed conditions (4-fold for NF filter, 15-fold for both 1000 FD and 900DD). It is noted that these results could be due to the enriched stem/progenitor populations demonstrated earlier in processed conditions and/or increased mechanical forces experienced during processing.

Material & Methods

Emulsification Device Fabrication

Devices 10 were 3D printed by Dinsmore Inc. (Irvine, CA) using an SLA 3D printer. Devices were printed using biocompatible Somos® BioClear resin from Royal DSM (Elgin, Illinois). The expansion region 22 and constriction regions 18, 20, as well as the luer inlet port 12 and outlet port 14 were printed as a single monolithic part 11.

Emulsification Device Operation

Lipoaspirate (LA) 4 was obtained from the abdomen and flanks of patients using standard vacuum-assisted liposuction. LA was combined with sterile phosphate-buffered saline (PBS) and washed repeatedly until golden in color. 10 mL of washed LA was loaded into a syringe and connected to the luer inlet 12 of the emulsification device 10. A collection syringe 94 was connected to the luer outlet 14 of the device 10. LA was passed back and forth through the device 10, 20, or 30 times using a syringe pump set to 20 mL/s. Samples were then prepared for SVF isolation, cell counts, and flow cytometry staining and analysis.

Stromal Vascular Fraction Isolation

All samples were processed for SVF isolation following a method previously described in literature. See e.g., Banyard et al., Implications for human adipose-derived stem cells in plastic surgery. J. Cell. Mol. Med. 19, 21-30 (2015), which is incorporated herein by reference. Briefly, 0.1% type I collagenase (Sigma-Aldrich Co., St. Louis, MO) was prepared in PBS, sterilized using a 0.22 μm vacuum filter (Millipore Corp., Billerica, MA), mixed with LA at a 1:1 ratio, and incubated at 37° C. for 30 min in a hot water bath, swirling intermittently. Control media (DMEM supplemented with 10% fetal bovine serum, 500 IU penicillin and 500 μg streptomycin) was then added in an equal volume to neutralize enzymatic activity. Mixture was allowed to separate for 10 minutes, and the infranatant layer that contains the SVF was collected and filtered through a 100 μm cell strainer. Samples were centrifuged at 500×g for 7 min and pellets were resuspended in control media.

Analysis of Single Cells Using Flow Cytometry

Collagenase digested cell suspensions were evenly divided into FACS tubes and resuspended in FACS Buffer (lx PBS, without Ca and Mg cations) supplemented with 1% BSA (PBS+). Cell suspensions were stained simultaneously with 5 μL (1 test) of each of the following monoclonal mouse anti-human antibodies in 100 uL total volume: CD34-BV421 (clone 561), CD45-BV510 (clone 2D1), SSEA-3-FITC (clone MC-631), CD26-PE (clone BASb), CD31-PE/Cy7 (clone WM59), CD55-APC (clone JS11), CD13-APC/Cy7 (clone WM15) for 20 minutes at 4° C. and washed once with FACS Buffer by centrifugation. All antibodies were purchased from BioLegend, San Diego, CA Cells were then resuspended in PBS+ supplemented with 7-AAD (BD Biosciences, San Jose, CA) and maintained on ice for at least 15 minutes prior to analysis on a Novocyte 3000 Flow Cytometer (ACEA Biosciences, San Diego, CA). Compensation was determined using single antibody stained samples of compensation beads (Invitrogen, Waltham, MA) and a live and dead (heat-killed at 55° C. for 15 min) cell sample stained with 7-AAD. Gates encompassing the positive and negative subpopulations within each compensation sample were inputted into FlowJo to automatically calculate the compensation matrix. Compensated data was then analyzed using FlowJo software (FlowJo, Ashland, OR). Signal positivity was determined using appropriate Fluorescence Minus One (FMO) controls. A sequential gating scheme (FIG. 10) was used to identify cell populations of interest from non-cellular debris and cellular aggregates.

Microfluidic Filter Device Fabrication

Microfluidic filter devices 30 were fabricated by ALine, Inc. (Rancho Dominguez, CA). Briefly, fluidic chambers 36, channels 40, 41, openings 42 for membranes, luers 34, 38, and hose barbs 46, and vias 48 were micro-machined into acrylic layers using a $CO_2$ laser. Nylon mesh membranes 44 with 500 and 1,000 μm pore sizes were purchased from Amazon Small Parts (Seattle, WA) as large sheets and were cut to appropriate size using a $CO_2$ laser. Device layers 32*a-f*, nylon mesh membranes 44, luers 34, 38, and hose barbs 46 were then assembled, bonded using adhesive, and pressure laminated to form a single monolithic device (FIG. 5B).

Microfluidic Filter Device Operation

Prior to introduction to the microfluidic filter devices 30, LA was processed using the emulsification device 10 for thirty (30) passes, as previously described. A syringe loaded with this processed sample was then connected to the luer inlet 34 of the microfluidic filter device 30. Sample was passed through the microfluidic filter device 30 using a syringe pump 90 at 10 mL/min. Microfluidic filter devices 30 were operated under direct filtration with the cross-flow outlet 38 closed, in order to maximize sample recovery and processing speed. For device operation, the cross-flow outlet 38 was closed off using a stop cock, and sample passed from the device inlet 34, through the membrane 44, and exited the effluent outlet 46. Filtered samples 100 were collected from the effluent outlet 46, and prepared for SVF isolation, cell counts and flow cytometry staining and analysis

Microfluidic Dissociation Device Fabrication and Operation

Microfluidic dissociation devices 60 were 3D printed by 3D Systems (Rock Hill, SC), using their biocompatible Accura ClearVue resin. The branching network of channels 64, 66, 70, 72 in this device, as well as the luer inlet port 62 and luer outlet port 68 were printed as a single part. Channel height was constant at 750 μm throughout the branching network of channels 64, 66, 70, 72. With each channel bifurcation, the minimum channel width halved, from 3 mm to 1.5 mm to 750 μm.

For microfluidic dissociation device 60 testing, LA samples 4 are mechanically processed using 30 passes through the emulsification device 10 passes and then filtered using the 1,000 μm pore microfluidic filter device 30. Sample effluent 100 from the microfluidic filter device 30 was then be further processed using 100, 300, or 900 mL/min flow rates and 20 passes. Samples were collected and analyzed for cell counts, viability, stem/progenitor cell content, and population size using image analysis.

While embodiments of the present invention have been shown and described, various modifications may be made without departing from the scope of the present invention. The invention, therefore, should not be limited except to the following claims and their equivalents.

What is claimed is:

1. An emulsification device for processing lipoaspirate comprising:

a substrate having an inlet and an outlet and a fluid passageway extending between the inlet and the outlet;

a first constriction region formed in the fluid passageway adjacent to the inlet;

a second constriction region formed in the fluid passageway adjacent to the outlet; and an expansion region formed in the fluid passageway between the first constriction region and the second constriction region, wherein the expansion region is formed in multiple planes, such that an angled wall or a surface of the expansion region extends in three dimensions, and the expansion region is configured for turbulent mixing; and wherein the first constriction region and the second constriction region have a cross-sectional dimension of between 0.5 mm and 4 mm and wherein the expansion region has a maximum cross-sectional dimension within the range of range of about 5 mm to about 30 mm.

2. The emulsification device of claim 1, wherein the first constriction region and the second constriction region have the same cross-sectional dimensions.

3. The emulsification device of claim 1, wherein the first constriction region and the second constriction region have a cross-sectional dimension of between 1 mm and 2 mm.

4. The emulsification device of claim 1, wherein the expansion region has a maximum cross-sectional dimension within the range of range of about 10 mm to about 20 mm.

5. The emulsification device of claim 1, wherein the expansion region comprises an abrupt expansion defined by the angled wall or surface.

6. The emulsification device of claim 1, wherein the substrate is a monolithic substrate.

7. A method of using the device of claim 1, comprising flowing lipoaspirate between the inlet and the outlet a plurality of times.

8. The emulsification device of claim 1, wherein the expansion region has a circular cross section oriented perpendicular to the fluid passageway.

9. The emulsification device of claim 1, wherein the angled wall or surface of the expansion region expanding in three dimensions expands from the first constriction and from the second constriction and reaches a maximum expansion substantially in a middle of the emulsification device.

10. The emulsification device of claim 1, wherein the angled wall or surface of the expansion region expanding in three dimensions expands from the first constriction and from the second constriction in a symmetrical configuration.

* * * * *